(12) United States Patent
Chhikara et al.

(10) Patent No.: US 11,744,775 B2
(45) Date of Patent: Sep. 5, 2023

(54) PRESSURE-REGULATING VIAL ACCESS DEVICES AND METHODS

(71) Applicant: ICU Medical, Inc., San Clemente, CA (US)

(72) Inventors: Bhupinder Chhikara, San Clemente, CA (US); Srinath Lingutla, San Clemente, CA (US); Brandon Eads, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 822 days.

(21) Appl. No.: 16/370,554

(22) Filed: Mar. 29, 2019

(65) Prior Publication Data

US 2019/0358125 A1 Nov. 28, 2019

Related U.S. Application Data

(63) Continuation of application No. PCT/US2017/053792, filed on Sep. 27, 2017.
(Continued)

(51) Int. Cl.
*A61J 1/20* (2006.01)
*A61J 1/14* (2023.01)

(52) U.S. Cl.
CPC ............ *A61J 1/201* (2015.05); *A61J 1/1406* (2013.01); *A61J 1/2089* (2013.01); *A61J 1/2055* (2015.05);
(Continued)

(58) Field of Classification Search
CPC ............ A61J 1/20–2096; A61M 39/10; A61M 2039/1072
See application file for complete search history.

(56) References Cited

U.S. PATENT DOCUMENTS

| 2,074,223 A | 3/1937 | Horiuchi et al. |
| 2,409,734 A | 10/1946 | Bucher et al. |

(Continued)

FOREIGN PATENT DOCUMENTS

| AU | 2013200393 A1 | 2/2013 |
| CA | 1037428 | 8/1978 |

(Continued)

OTHER PUBLICATIONS

U.S. Appl. No. 15/483,446, filed Apr. 10, 2017, Fangrow.
(Continued)

*Primary Examiner* — Benjamin J Klein

(74) *Attorney, Agent, or Firm* — Knobbe, Martens, Olson & Bear, LLP

(57) ABSTRACT

In certain embodiments, a vial access device for removing liquid contents from a vial includes a piercing member extending from a base of an insertion member and a reservoir. The reservoir can be contained within the piercing member and the insertion member, such that the reservoir is introduced to the vial when piercing member is inserted into the vial. The piercing member is adapted to be opened inside the vial to expose the reservoir to the contents inside the vial. A locking mechanism can prevent the piercing member from being inserted into the vial unless the vial access device is fully coupled to the vial and/or prevent the piercing member from being withdrawn from the vial without uncoupling the vial access device from the vial.

31 Claims, 14 Drawing Sheets

Related U.S. Application Data

(60) Provisional application No. 62/402,593, filed on Sep. 30, 2016.

(52) U.S. Cl.
CPC ............ *A61J 1/2068* (2015.05); *A61J 1/2079* (2015.05); *A61J 1/2096* (2013.01)

(56) References Cited

U.S. PATENT DOCUMENTS

| | | |
|---|---|---|
| 2,419,401 A | 4/1947 | Hinds |
| 2,668,533 A | 2/1954 | Evans |
| 2,673,013 A | 3/1954 | Hester |
| 2,852,024 A | 7/1954 | Ryan |
| 2,793,758 A | 3/1961 | Murrish |
| 2,999,499 A | 9/1961 | Willet |
| 2,999,500 A | 9/1961 | Schurer |
| 3,291,151 A | 12/1966 | Loken |
| RE26,488 E | 11/1968 | Bull |
| 3,542,240 A | 11/1970 | Solowey |
| 3,557,778 A | 1/1971 | Hughes |
| 3,584,770 A | 6/1971 | Taylor |
| 3,797,521 A | 3/1974 | King |
| 3,822,700 A | 7/1974 | Pennington |
| 3,844,283 A | 10/1974 | Dabney |
| 3,853,157 A | 12/1974 | Madaio |
| 3,923,058 A | 12/1975 | Weingarten |
| 3,938,520 A | 2/1976 | Scislowcz et al. |
| 3,940,003 A | 2/1976 | Larson |
| 3,941,167 A | 3/1976 | Haury-Wirtz et al. |
| 3,957,082 A | 5/1976 | Fuson et al. |
| 3,980,082 A | 9/1976 | Miller |
| 3,993,063 A | 11/1976 | Larrabee |
| 4,046,291 A | 9/1977 | Goda |
| 4,058,121 A | 11/1977 | Choski et al. |
| 4,143,853 A | 3/1979 | Abramson |
| 4,207,923 A | 6/1980 | Giurtino |
| 4,219,021 A | 8/1980 | Fink |
| 4,240,433 A | 12/1980 | Bordow |
| 4,240,833 A | 12/1980 | Myles |
| 4,253,459 A | 3/1981 | Willis |
| 4,262,671 A | 4/1981 | Kersten |
| 4,301,799 A | 11/1981 | Pope, Jr. et al. |
| 4,312,349 A | 1/1982 | Cohen |
| 4,314,586 A | 2/1982 | Folkman |
| 4,334,551 A | 6/1982 | Pfister |
| 4,349,035 A | 9/1982 | Thomas et al. |
| 4,376,634 A | 3/1983 | Prior et al. |
| 4,381,776 A | 5/1983 | Latham, Jr. |
| 4,396,016 A | 8/1983 | Becker |
| 4,410,321 A | 10/1983 | Pearson et al. |
| 4,458,733 A | 7/1984 | Lyons |
| 4,475,915 A | 10/1984 | Sloane |
| 4,493,348 A | 1/1985 | Lemmons |
| 4,505,709 A | 3/1985 | Froning et al. |
| 4,534,758 A | 8/1985 | Akers et al. |
| 4,564,054 A | 1/1986 | Gustavsson |
| 4,573,993 A | 3/1986 | Hoag et al. |
| 4,576,211 A | 3/1986 | Valentini et al. |
| 4,588,403 A | 5/1986 | Weiss et al. |
| 4,600,040 A | 7/1986 | Naslund |
| 4,645,073 A | 2/1987 | Homan |
| 4,673,404 A | 6/1987 | Gustavsson |
| 4,730,635 A | 3/1988 | Linden |
| 4,735,608 A | 4/1988 | Sardam |
| 4,743,243 A | 5/1988 | Vaillancourt |
| 4,768,568 A | 9/1988 | Fournier et al. |
| 4,785,859 A | 11/1988 | Gustavsson et al. |
| 4,798,578 A | 1/1989 | Ranford |
| 4,857,068 A | 8/1989 | Kahn |
| 4,929,230 A | 5/1990 | Pfleger |
| 4,981,464 A | 1/1991 | Suzuki |
| 5,006,114 A | 4/1991 | Rogers |
| 5,060,704 A | 10/1991 | Rohrbough |
| 5,169,393 A | 12/1992 | Moorehead et al. |
| 5,176,673 A | 1/1993 | Marrucchi |
| 5,334,163 A | 8/1994 | Sinnett |
| 5,349,984 A | 9/1994 | Weinheimer et al. |
| 5,405,331 A | 4/1995 | Behnke et al. |
| 5,445,630 A | 8/1995 | Richmond |
| 5,478,337 A | 12/1995 | Okamoto et al. |
| 5,580,351 A | 12/1996 | Helgren et al. |
| 5,660,796 A | 8/1997 | Sheehy |
| 5,685,866 A | 11/1997 | Lopez |
| 5,700,245 A | 12/1997 | Sancoff et al. |
| 5,725,500 A | 3/1998 | Micheler |
| 5,749,394 A | 5/1998 | Boehmer et al. |
| 5,766,147 A | 6/1998 | Sancoff et al. |
| 5,772,079 A | 6/1998 | Gueret |
| 5,776,125 A | 7/1998 | Dudar et al. |
| 5,803,311 A | 9/1998 | Fuchs |
| 5,833,213 A | 11/1998 | Ryan |
| 5,890,610 A | 4/1999 | Jansen et al. |
| 6,003,553 A | 12/1999 | Wahlberg |
| 6,071,270 A | 6/2000 | Fowles et al. |
| 6,139,534 A | 10/2000 | Niedospial et al. |
| 6,159,192 A | 12/2000 | Fowles et al. |
| 6,358,236 B1 | 3/2002 | DeFoggi et al. |
| 6,457,488 B2 | 10/2002 | Loo |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,572,256 B2 | 6/2003 | Seaton et al. |
| 6,679,290 B2 | 1/2004 | Matthews et al. |
| 6,692,478 B1 | 2/2004 | Paradis |
| 6,715,520 B2 | 4/2004 | Andreasson et al. |
| 6,719,719 B2 | 4/2004 | Carmel et al. |
| 6,890,328 B2 | 5/2005 | Fowles et al. |
| 6,989,002 B2 | 1/2006 | Guala |
| 6,997,910 B2 | 2/2006 | Howlett et al. |
| 6,997,917 B2 | 2/2006 | Niedospial, Jr. et al. |
| 7,004,926 B2 | 2/2006 | Navia et al. |
| 7,048,720 B1 | 5/2006 | Thorne, Jr. et al. |
| 7,086,431 B2 | 8/2006 | D'Antonio et al. |
| 7,101,354 B2 | 9/2006 | Thorne, Jr. et al. |
| 7,140,401 B2 | 11/2006 | Wilcox et al. |
| 7,192,423 B2 | 3/2007 | Wong |
| 7,213,702 B2 | 5/2007 | Takimoto et al. |
| 7,291,131 B2 | 11/2007 | Call |
| 7,306,584 B2 | 12/2007 | Wessman et al. |
| 7,354,427 B2 | 4/2008 | Fangrow |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,408 B2 | 11/2009 | Yandell |
| 7,632,261 B2 | 12/2009 | Zinger et al. |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,703,486 B2 | 4/2010 | Costanzo |
| 7,731,678 B2 | 6/2010 | Tennican et al. |
| 7,743,799 B2 | 6/2010 | Mosler et al. |
| 7,744,580 B2 | 6/2010 | Reboul |
| 7,758,560 B2 | 7/2010 | Connell et al. |
| 7,789,871 B1 | 9/2010 | Yandell |
| D630,732 S | 1/2011 | Lev et al. |
| 7,862,537 B2 | 1/2011 | Zinger et al. |
| 7,879,018 B2 | 2/2011 | Zinger et al. |
| 7,883,499 B2 | 2/2011 | Fangrow |
| 7,887,528 B2 | 2/2011 | Yandell |
| 7,900,659 B2 | 3/2011 | Whitley et al. |
| D637,713 S | 5/2011 | Nord et al. |
| 7,963,954 B2 | 6/2011 | Kavazov |
| D641,080 S | 7/2011 | Zinger et al. |
| 7,972,321 B2 | 7/2011 | Fangrow |
| 7,981,089 B2 | 7/2011 | Weilbacher |
| 7,981,101 B2 | 7/2011 | Walsh |
| 7,998,106 B2 | 8/2011 | Thorne, Jr. et al. |
| 8,021,325 B2 | 9/2011 | Zinger et al. |

(56) References Cited

U.S. PATENT DOCUMENTS

| | | |
|---|---|---|
| 8,025,653 B2 | 9/2011 | Capitqaine et al. |
| 8,029,747 B2 | 10/2011 | Helmerson |
| 8,074,964 B2 | 12/2011 | Mansour et al. |
| 8,100,154 B2 | 1/2012 | Reynolds et al. |
| 8,109,285 B2 | 2/2012 | Ehrman et al. |
| 8,122,923 B2 | 2/2012 | Kraus et al. |
| 8,123,736 B2 | 2/2012 | Kraushaar et al. |
| 8,141,601 B2 | 3/2012 | Fehr et al. |
| 8,156,971 B2 | 4/2012 | Costanzo |
| 8,162,006 B2 | 4/2012 | Guala |
| 8,162,013 B2 | 4/2012 | Rosenquist et al. |
| 8,162,914 B2 | 4/2012 | Kraushaar et al. |
| 8,167,863 B2 | 5/2012 | Yow |
| 8,167,864 B2 | 5/2012 | Browne |
| 8,172,794 B2 | 5/2012 | Lum et al. |
| 8,177,768 B2 | 5/2012 | Leinsing |
| 8,196,614 B2 | 6/2012 | Kriheli |
| 8,197,459 B2 | 6/2012 | Jansen et al. |
| 8,206,367 B2 | 6/2012 | Warren et al. |
| 8,211,082 B2 | 7/2012 | Hasegawa et al. |
| 8,221,382 B2 | 7/2012 | Moy et al. |
| 8,225,826 B2 | 7/2012 | Horppu et al. |
| 8,231,567 B2 | 7/2012 | Tennican et al. |
| 8,241,265 B2 | 8/2012 | Moy et al. |
| 8,262,643 B2 | 9/2012 | Tennican |
| 8,267,127 B2 | 9/2012 | Kriheli |
| 8,267,913 B2 | 9/2012 | Fangrow |
| 8,281,807 B2 | 10/2012 | Trombley, III et al. |
| 8,286,936 B2 | 10/2012 | Kitani et al. |
| 8,287,513 B2 | 10/2012 | Ellstrom et al. |
| 8,336,587 B2 | 12/2012 | Rosenquist et al. |
| 8,356,644 B2 | 1/2013 | Chong et al. |
| 8,356,645 B2 | 1/2013 | Chong et al. |
| 8,357,137 B2 | 1/2013 | Yandell |
| 8,381,776 B2 | 2/2013 | Horppu |
| 8,403,905 B2 | 3/2013 | Yow |
| 8,409,164 B2 | 4/2013 | Fangrow |
| 8,409,165 B2 | 4/2013 | Niedospial et al. |
| 8,414,554 B2 | 4/2013 | Garfield et al. |
| 8,414,555 B2 | 4/2013 | Garfield et al. |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 8,469,939 B2 | 6/2013 | Fangrow |
| 8,506,548 B2 | 8/2013 | Okiyama |
| 8,511,352 B2 | 8/2013 | Kraus et al. |
| 8,512,307 B2 | 8/2013 | Fangrow |
| 8,522,832 B2 | 9/2013 | Lopez et al. |
| 8,523,838 B2 | 9/2013 | Tornqvist |
| 8,540,692 B2 | 9/2013 | Fangrow |
| 8,602,067 B2 | 12/2013 | Kuhni et al. |
| 8,608,723 B2 | 12/2013 | Lev et al. |
| 8,622,985 B2 | 1/2014 | Ellstrom |
| 8,657,803 B2 | 2/2014 | Helmerson et al. |
| 8,667,996 B2 | 3/2014 | Gonnelli et al. |
| 8,684,992 B2 | 4/2014 | Sullivan et al. |
| 8,684,994 B2 | 4/2014 | Lev et al. |
| 8,701,696 B2 | 4/2014 | Guala |
| 8,702,675 B2 | 4/2014 | Imai |
| 8,720,496 B2 | 5/2014 | Huwiler et al. |
| 8,721,614 B2 | 5/2014 | Takemoto et al. |
| 8,753,325 B2 | 6/2014 | Lev et al. |
| 8,795,231 B2 | 8/2014 | Chong et al. |
| 8,801,678 B2 | 8/2014 | Panian et al. |
| 8,821,436 B2 | 9/2014 | Mosler et al. |
| 8,827,977 B2 | 9/2014 | Fangrow |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,870,846 B2 | 10/2014 | Davis et al. |
| 8,882,738 B2 | 11/2014 | Fangrow et al. |
| 8,900,212 B2 | 12/2014 | Kubo |
| 8,910,919 B2 | 12/2014 | Bonnal et al. |
| 8,926,554 B2 | 1/2015 | Okuda et al. |
| 8,945,084 B2 | 2/2015 | Warren et al. |
| 8,973,622 B2 | 3/2015 | Lopez |
| 8,974,433 B2 | 3/2015 | Fangrow |
| 8,986,262 B2 | 3/2015 | Young et al. |
| 8,992,501 B2 | 3/2015 | Siefert et al. |
| 9,005,179 B2 | 4/2015 | Fangrow et al. |
| 9,005,180 B2 | 4/2015 | Siefert et al. |
| 9,060,921 B2 | 6/2015 | Siefert et al. |
| 9,067,049 B2 | 6/2015 | Panian et al. |
| 9,072,657 B2 | 7/2015 | Siefert et al. |
| 9,089,474 B2 | 7/2015 | Cederschiöld |
| 9,089,475 B2 | 7/2015 | Fangrow |
| 9,107,808 B2 | 8/2015 | Fangrow |
| 9,132,062 B2 | 9/2015 | Fangrow |
| 9,132,063 B2 | 9/2015 | Lev et al. |
| 9,144,646 B2 | 9/2015 | Barron, III et al. |
| 9,198,832 B2 | 12/2015 | Moy et al. |
| 9,205,248 B2 | 12/2015 | Wu et al. |
| 9,211,231 B2 | 12/2015 | Mansour et al. |
| 9,237,986 B2 | 1/2016 | Mansour et al. |
| 9,278,206 B2 | 3/2016 | Fangrow |
| 9,345,640 B2 | 5/2016 | Mosler et al. |
| 9,345,641 B2 | 5/2016 | Kraus et al. |
| 9,351,905 B2 | 5/2016 | Fangrow et al. |
| 9,358,182 B2 | 6/2016 | Garfield et al. |
| 9,370,466 B2 | 6/2016 | Garfield et al. |
| 9,381,135 B2 | 7/2016 | Reynolds et al. |
| 9,381,137 B2 | 7/2016 | Garfield et al. |
| 9,381,339 B2 | 7/2016 | Wu et al. |
| 9,440,060 B2 | 9/2016 | Fangrow |
| 9,511,989 B2 | 12/2016 | Lopez |
| 9,572,750 B2 | 2/2017 | Mansour et al. |
| 9,585,812 B2 | 3/2017 | Browka et al. |
| 9,597,260 B2 | 3/2017 | Ivosevic |
| 9,610,217 B2 | 4/2017 | Fangrow |
| 9,615,997 B2 | 4/2017 | Fangrow |
| 9,662,272 B2 | 5/2017 | Warren et al. |
| 9,763,855 B2 | 9/2017 | Fangrow et al. |
| 9,827,163 B2 | 11/2017 | Lopez et al. |
| 9,895,291 B2 | 2/2018 | Fangrow |
| 9,931,275 B2 | 4/2018 | Fangrow |
| 9,931,276 B2 | 4/2018 | Lopez |
| 9,987,195 B2 | 6/2018 | Fangrow |
| 9,993,390 B2 | 6/2018 | Seifert et al. |
| 9,993,391 B2 | 6/2018 | Warren et al. |
| 9,999,569 B2 | 6/2018 | Kriheli |
| 10,016,339 B2 | 7/2018 | Guala |
| 10,022,302 B2 | 7/2018 | Warran et al. |
| 10,071,020 B2 | 9/2018 | Warren et al. |
| 10,086,188 B2 | 10/2018 | Fangrow |
| 10,117,807 B2 | 11/2018 | Fangrow |
| 10,201,476 B2 | 2/2019 | Fangrow |
| 10,292,904 B2 | 5/2019 | Fangrow |
| 10,299,989 B2 | 5/2019 | Fangrow |
| 10,327,989 B2 | 6/2019 | Fangrow |
| 10,327,991 B2 | 6/2019 | Seifert et al. |
| 10,327,992 B2 | 6/2019 | Fangrow et al. |
| 10,327,993 B2 | 6/2019 | Fangrow et al. |
| 10,369,349 B2 | 8/2019 | Nelson |
| 10,391,293 B2 | 8/2019 | Fangrow |
| 10,406,072 B2 | 9/2019 | Chhikara et al. |
| 10,492,993 B2 | 12/2019 | Seifert et al. |
| 10,688,022 B2 | 6/2020 | Fangrow |
| 10,806,672 B2 | 10/2020 | Fangrow |
| 10,918,573 B2 | 2/2021 | Fangrow |
| 10,987,277 B2 | 4/2021 | Fangrow |
| 11,013,664 B2 | 5/2021 | Fangrow et al. |
| 11,129,773 B2 | 9/2021 | Fangrow |
| 11,185,471 B2 | 11/2021 | Fangrow |
| 11,504,302 B2 | 11/2022 | Chhikara et al. |
| 11,529,289 B2 | 12/2022 | Fangrow |
| 2002/0095133 A1 | 7/2002 | Gillis et al. |
| 2002/0193777 A1* | 12/2002 | Aneas .............. A61J 1/2096 604/411 |
| 2003/0153895 A1 | 8/2003 | Leinsing |
| 2003/0216695 A1 | 11/2003 | Yang |
| 2003/0229330 A1 | 12/2003 | Hickle |
| 2004/0073169 A1 | 4/2004 | Amisar et al. |
| 2004/0073189 A1 | 4/2004 | Wyatt et al. |
| 2005/0087715 A1 | 4/2005 | Doyle |

(56) References Cited

U.S. PATENT DOCUMENTS

| | | |
|---|---|---|
| 2005/0131357 A1 | 6/2005 | Denton et al. |
| 2005/0148992 A1 | 7/2005 | Simas, Jr. et al. |
| 2005/0203481 A1 | 9/2005 | Orlu et al. |
| 2006/0025747 A1 | 2/2006 | Sullivan et al. |
| 2006/0111667 A1 | 5/2006 | Matsuura et al. |
| 2006/0149309 A1 | 7/2006 | Paul et al. |
| 2006/0184103 A1 | 8/2006 | Paproski et al. |
| 2006/0184139 A1 | 8/2006 | Quigley et al. |
| 2007/0071243 A1 | 3/2007 | Nanda |
| 2007/0093775 A1 | 4/2007 | Daly |
| 2007/0112324 A1 | 5/2007 | Hamedi-Sangsari |
| 2007/0208320 A1 | 9/2007 | Muramatsu et al. |
| 2008/0045919 A1 | 2/2008 | Jakob et al. |
| 2008/0067462 A1 | 3/2008 | Miller et al. |
| 2008/0140021 A1* | 6/2008 | Richmond ............ A61M 39/26 604/246 |
| 2008/0172003 A1 | 7/2008 | Plishka et al. |
| 2008/0208159 A1 | 8/2008 | Stanus et al. |
| 2008/0287914 A1* | 11/2008 | Wyatt ................... A61J 1/2096 604/319 |
| 2009/0057258 A1 | 3/2009 | Tornqvist |
| 2009/0069783 A1* | 3/2009 | Ellstrom ............... A61J 1/2089 604/414 |
| 2010/0000035 A1 | 1/2010 | Lee |
| 2010/0059474 A1 | 3/2010 | Brandenburger et al. |
| 2010/0106129 A1* | 4/2010 | Goeckner ............. A61J 1/2089 604/411 |
| 2010/0160889 A1 | 6/2010 | Smith et al. |
| 2010/0179506 A1 | 7/2010 | Shemesh et al. |
| 2010/0249723 A1 | 9/2010 | Fangrow, Jr. |
| 2010/0305548 A1 | 12/2010 | Kraushaar |
| 2011/0004183 A1 | 1/2011 | Carrez et al. |
| 2011/0125104 A1 | 5/2011 | Lynn |
| 2011/0125128 A1 | 5/2011 | Nord et al. |
| 2011/0175347 A1 | 7/2011 | Okiyama |
| 2011/0184382 A1 | 7/2011 | Cady |
| 2011/0208128 A1 | 8/2011 | Wu et al. |
| 2011/0224611 A1 | 9/2011 | Lum et al. |
| 2011/0240158 A1 | 10/2011 | Py |
| 2011/0257621 A1 | 10/2011 | Fangrow |
| 2011/0264037 A1* | 10/2011 | Foshee .................. A61M 11/00 604/82 |
| 2012/0046636 A1* | 2/2012 | Kriheli ................. A61J 1/2096 604/414 |
| 2012/0059346 A1 | 3/2012 | Sheppard et al. |
| 2012/0067429 A1 | 3/2012 | Mosler et al. |
| 2012/0078091 A1 | 3/2012 | Suchecki |
| 2012/0078214 A1 | 3/2012 | Finke et al. |
| 2012/0078215 A1 | 3/2012 | Finke et al. |
| 2012/0109077 A1 | 5/2012 | Ryan |
| 2012/0157964 A1 | 6/2012 | Haimi |
| 2012/0172830 A1 | 7/2012 | Yokoyama et al. |
| 2012/0215181 A1 | 8/2012 | Lee |
| 2012/0220978 A1 | 8/2012 | Lev et al. |
| 2012/0298254 A1 | 11/2012 | Brem et al. |
| 2012/0302986 A1 | 11/2012 | Brem et al. |
| 2013/0033034 A1 | 2/2013 | Trombley, III et al. |
| 2013/0053814 A1 | 2/2013 | Mucientes et al. |
| 2013/0053815 A1 | 2/2013 | Mucientes et al. |
| 2013/0060226 A1 | 3/2013 | Fini et al. |
| 2013/0066293 A1 | 3/2013 | Garfield et al. |
| 2013/0110053 A1 | 5/2013 | Yoshino et al. |
| 2013/0130197 A1 | 5/2013 | Jessop et al. |
| 2013/0180618 A1 | 7/2013 | Py |
| 2013/0199669 A1 | 8/2013 | Moy et al. |
| 2013/0218121 A1 | 8/2013 | Waller et al. |
| 2013/0226099 A1 | 8/2013 | Fangrow |
| 2013/0228239 A1 | 9/2013 | Cederschiöld |
| 2013/0231630 A1 | 9/2013 | Kraus et al. |
| 2013/0306169 A1 | 11/2013 | Weibel |
| 2014/0000738 A1 | 1/2014 | Reynolds et al. |
| 2014/0014210 A1 | 1/2014 | Cederschiöld |
| 2014/0020792 A1 | 1/2014 | Kraus et al. |
| 2014/0107588 A1 | 4/2014 | Fangrow |
| 2014/0124087 A1 | 5/2014 | Anderson et al. |
| 2014/0124092 A1 | 5/2014 | Gonnelli et al. |
| 2014/0150925 A1 | 6/2014 | Sjogren et al. |
| 2014/0261727 A1 | 8/2014 | Mansour et al. |
| 2014/0261860 A1 | 9/2014 | Heath et al. |
| 2014/0261876 A1 | 9/2014 | Mansour et al. |
| 2014/0261877 A1 | 9/2014 | Ivosevic et al. |
| 2014/0276386 A1 | 9/2014 | Mansour et al. |
| 2014/0276649 A1 | 9/2014 | Ivosevic et al. |
| 2015/0065987 A1 | 3/2015 | Fangrow |
| 2015/0068640 A1 | 3/2015 | Garfield et al. |
| 2015/0082746 A1 | 3/2015 | Ivosevic et al. |
| 2015/0123398 A1 | 5/2015 | Sanders et al. |
| 2015/0126958 A1 | 5/2015 | Sanders et al. |
| 2015/0157848 A1 | 6/2015 | Wu et al. |
| 2015/0209230 A1 | 7/2015 | Lev et al. |
| 2015/0209232 A1* | 7/2015 | Haindl .................. A61J 1/20 604/411 |
| 2015/0209233 A1 | 7/2015 | Fukuoka |
| 2015/0209572 A1 | 7/2015 | Garfield et al. |
| 2015/0250680 A1 | 9/2015 | Browka et al. |
| 2015/0250681 A1 | 9/2015 | Lev et al. |
| 2015/0265500 A1 | 9/2015 | Russo et al. |
| 2015/0297451 A1 | 10/2015 | Marici et al. |
| 2015/0297453 A1 | 10/2015 | Kim et al. |
| 2015/0297454 A1* | 10/2015 | Sanders ............... A61J 1/2055 604/414 |
| 2015/0297456 A1 | 10/2015 | Marici et al. |
| 2015/0297459 A1 | 10/2015 | Sanders et al. |
| 2015/0297817 A1 | 10/2015 | Guala |
| 2015/0297839 A1 | 10/2015 | Sanders et al. |
| 2015/0320992 A1 | 11/2015 | Bonnett et al. |
| 2015/0359709 A1 | 12/2015 | Kriheli et al. |
| 2015/0366758 A1 | 12/2015 | Noguchi et al. |
| 2016/0000653 A1 | 1/2016 | Kramer |
| 2016/0008534 A1 | 1/2016 | Cowan et al. |
| 2016/0038373 A1 | 2/2016 | Ohlin |
| 2016/0038374 A1 | 2/2016 | Merhold et al. |
| 2016/0051446 A1 | 2/2016 | Lev et al. |
| 2016/0058667 A1 | 3/2016 | Kriheli |
| 2016/0081878 A1 | 3/2016 | Marks et al. |
| 2016/0081879 A1 | 3/2016 | Garfield et al. |
| 2016/0101020 A1 | 4/2016 | Guala |
| 2016/0106970 A1 | 4/2016 | Fangrow |
| 2016/0136051 A1 | 5/2016 | Lavi |
| 2016/0136412 A1 | 5/2016 | McKinnon et al. |
| 2016/0206511 A1 | 7/2016 | Garfield et al. |
| 2016/0206512 A1 | 7/2016 | Chhikara et al. |
| 2016/0213568 A1 | 7/2016 | Mansour et al. |
| 2016/0250102 A1 | 9/2016 | Garfield et al. |
| 2016/0262981 A1 | 9/2016 | Carrez et al. |
| 2016/0262982 A1* | 9/2016 | Cederschiöld ........ A61J 1/2072 |
| 2017/0007501 A1* | 1/2017 | Schuldt-Lieb ........ A61J 1/1406 |
| 2017/0027820 A1* | 2/2017 | Okiyama ............... A61J 1/201 |
| 2017/0095404 A1 | 4/2017 | Fangrow |
| 2017/0196772 A1 | 7/2017 | Seifert |
| 2017/0196773 A1 | 7/2017 | Fangrow |
| 2017/0202742 A1 | 7/2017 | Cheng et al. |
| 2017/0202744 A1 | 7/2017 | Fangrow |
| 2017/0202745 A1 | 7/2017 | Seifert |
| 2017/0239140 A1 | 8/2017 | Fangrow |
| 2017/0258682 A1 | 9/2017 | Kriheli |
| 2017/0296431 A1 | 10/2017 | Fangrow |
| 2017/0312176 A1 | 11/2017 | Fangrow |
| 2017/0333288 A1 | 11/2017 | Fangrow |
| 2018/0028402 A1 | 2/2018 | Kriheli et al. |
| 2018/0099137 A1 | 4/2018 | Fangrow |
| 2018/0125759 A1 | 5/2018 | Fangrow |
| 2018/0161245 A1 | 6/2018 | Kriheli |
| 2018/0193227 A1 | 7/2018 | Marci et al. |
| 2018/0207063 A1 | 7/2018 | Lopez et al. |
| 2018/0221572 A1 | 8/2018 | Schlitt et al. |
| 2018/0250195 A1 | 9/2018 | Fangrow |
| 2018/0280240 A1 | 10/2018 | Fangrow |
| 2019/0001114 A1 | 1/2019 | Fangrow |
| 2019/0117515 A1 | 4/2019 | Fangrow |
| 2019/0254926 A1 | 8/2019 | Seifert |
| 2019/0269900 A1 | 9/2019 | Fangrow |
| 2019/0350812 A1 | 11/2019 | Chhikara |

(56) References Cited

U.S. PATENT DOCUMENTS

| | | |
|---|---|---|
| 2020/0006372 A1 | 1/2020 | Zhang et al. |
| 2020/0038293 A1 | 2/2020 | Chhikara et al. |
| 2020/0069519 A1 | 3/2020 | Fangrow |
| 2020/0069520 A1 | 3/2020 | Fangrow |
| 2020/0093695 A1 | 3/2020 | Seifert |
| 2020/0337948 A1 | 10/2020 | Fangrow |
| 2021/0106499 A1 | 4/2021 | Fangrow |
| 2021/0228444 A1 | 7/2021 | Fangrow |
| 2021/0353500 A1 | 11/2021 | Warren |
| 2022/0071848 A1 | 3/2022 | Fangrow |
| 2022/0079843 A1 | 3/2022 | Fangrow |
| 2023/0075991 A1 | 3/2023 | Chhikara |

FOREIGN PATENT DOCUMENTS

| | | |
|---|---|---|
| CN | 101801440 A | 8/2010 |
| EP | 0 829 250 | 3/1998 |
| GB | 2 000 685 | 1/1979 |
| JP | 39-17386 | 8/1961 |
| JP | 45-20604 | 8/1970 |
| JP | 57-208362 | 12/1982 |
| JP | H02-193677 | 7/1990 |
| JP | H06-66682 | 9/1994 |
| JP | 2001-505083 | 4/2001 |
| JP | 2012-228332 | 11/2012 |
| JP | 2014-511249 | 5/2014 |
| JP | 2015-077217 | 4/2015 |
| JP | 2015-211763 | 11/2015 |
| RU | 2264231 | 2/2005 |
| WO | WO 1984/004673 | 12/1984 |
| WO | WO 1997/02853 | 1/1997 |
| WO | WO 2000/035517 | 6/2000 |
| WO | WO 2005/065626 | 7/2005 |
| WO | WO 2008/129550 | 10/2008 |
| WO | WO 2008/153460 | 12/2008 |
| WO | WO 2010/069359 | 6/2010 |
| WO | WO 2010/093581 | 8/2010 |
| WO | WO 2010/120953 | 10/2010 |
| WO | WO 2011/030787 | 3/2011 |
| WO | WO 2011/150037 | 12/2011 |
| WO | WO 2013/104736 | 7/2013 |
| WO | WO 2013/134246 | 9/2013 |
| WO | WO 2014/116602 | 7/2014 |
| WO | WO 2014/163851 | 10/2014 |
| WO | WO 2015/029018 | 3/2015 |
| WO | WO 2015/118432 | 8/2015 |
| WO | WO 2016/147178 | 9/2016 |
| WO | WO 2018/064206 | 4/2018 |
| WO | WO 2018/186361 | 10/2018 |

OTHER PUBLICATIONS

International Search Report and Written Opinion, re PCT Application No. PCT/US2017/053792, dated Jan. 2, 2018.
International Preliminary Reporton Patentability, re PCT Application No. PCT/US2017/053792, dated Apr. 2, 2019.
Clave—NeedleFree Connector, 2-page brochure. Jan. 2012 ICU Medical, Inc. (M1-1065 Rev. 04).
Equashield, Hazardous Drugs Closed System Transfer Device. Two webpages: http:/www.equashield.com, downloaded Jul. 22, 2013.
Genie—Closed Vial Access Device, 2-page brochure. Jan. 2012 ICU Medical, Inc. (M1-1186 Rev. 11).
OnGuard Contained Medication System with Tevadaptor Components, B. Braun Medical, Inc., Apr. 2007.
PhaSeal, The PhaSeal® Solution, http://www.phaseal.com/siteUS/page.asp?menuitem=145&right=0, dated Jan. 9, 2006.
PhaSeal, How to Use PhaSeal®, http://www.phaseal.com/siteUS/movies.asp?main=filmsmain&right=filmsright, dated Jul. 25, 2005.
"Protection Safety Products", IV Sets and Access Devices Medication Delivery Catalog, CHEMO-AIDE Dispensing Pin, Dec. 2002, pp. 7,21, Baxter Healthcare Corporation, Round Lake, IL.
Spiros—Closed Male Luer. 2-page brochure. Jan. 2012 ICU Medical, Inc. (M1-1184 Rev. 11).

\* cited by examiner

PRESSURE-REGULATING VIAL ACCESS DEVICES AND METHODS

INCORPORATION BY REFERENCE OF RELATED APPLICATIONS

This application is a continuation of PCT Patent Application No. PCT/US2017/053792, which claims priority to U.S. Provisional Patent Application No. 62/402,593, filed Sep. 30, 2016. The entire contents of both applications are incorporated by reference herein and made part of this specification.

BACKGROUND

Field

Certain embodiments disclosed herein relate to novel devices and methods for accessing medicinal fluids contained in containers, such as vials, and/or to aid in the injection of substances therein, while regulating pressure within such containers.

Description of Related Art

It is a common practice to store medicines or other medically related fluids in vials. In some instances, the medicines or fluids so stored are therapeutic if injected to the bloodstream, but harmful if inhaled or if contacted by exposed skin. Certain known systems for extracting potentially harmful medicines from vials suffer from various drawbacks.

SUMMARY

In some embodiments, a vial access device for accessing contents of a vial includes a housing including an insertion path and an insertion assembly including a piercing member. The insertion assembly can be configured to slide along the insertion path. The piercing member can be configured to pierce a septum of the vial.

In certain embodiments, a vial access device for removing liquid contents from a vial comprises a piercing member and a reservoir. The reservoir can be contained within the piercing member such that the reservoir is introduced to the vial when the piercing member enters the vial. In some embodiments, the reservoir expands within the vial as liquid is removed from the vial via the vial access device, thereby regulating pressure within the vial.

In some embodiments, a vial access device for removing liquid contents from a vial comprises a piercing member extending from a base of an insertion member and a reservoir. The reservoir can be contained within the piercing member and the insertion member. The piercing member end of the insertion member is configured to be inserted into the vial after the vial access device is coupled with the vial, such that the reservoir is introduced to the vial when the piercing member enters the vial. The piercing member is adapted to be expanded, separated, or opened inside the vial. The piercing member is configured to move from a first orientation substantially unexpanded, intact, or closed to a second orientation at least partially expanded, separated, or open and at least partially inside the vial. When the piercing member is in the second orientation the reservoir contained within the piercing member is exposed to the contents inside the vial. The piercing member is sized and positioned to at least partially fit within the vial when the piercing member is in the second orientation. The reservoir is also sized and positioned to at least partially fit within the vial when the piercing member is in the second orientation. The reservoir comprises a layer that is substantially impermeable to a medicinal fluid disposed within the vial, thereby impeding the passage of said medicinal fluid between an outer surface and an inner surface of the reservoir. The device regulates the pressure in the vial such that, as the medicinal fluid is withdrawn from (or added to) the vial, the reservoir will expand or contract in order to substantially equilibrate pressure on opposite sides of the reservoir.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments.

DETAILED DESCRIPTION OF CERTAIN EMBODIMENTS

Figure 1:
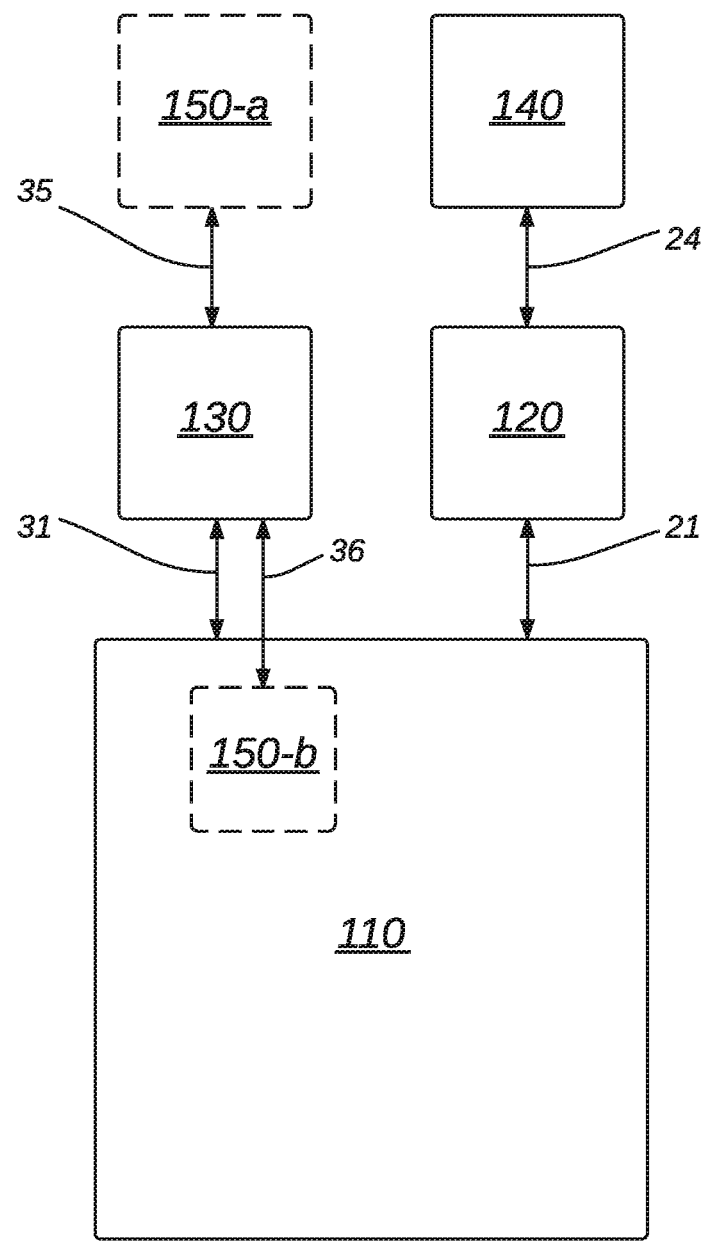
FIG. 1 is a schematic illustration of a system for removing fluid from and/or injecting fluid into a vial.

This disclosure relates to vial access devices that may be coupled to a container. The features of the vial access devices as described herein may be combined with any of the features of the embodiments described in U.S. Pat. No. 7,883,499, titled "VIAL ADAPTORS AND VIALS FOR REGULATION PRESSURE", filed Mar. 7, 2008, the entire contents of which are hereby incorporated by reference herein and are made a part of this specification. The features of the vial access devices as described herein may also be combined with any of the features of the embodiments described in U.S. Pat. No. 8,409,164, titled "ANTI-REFLUX VIAL ADAPTORS", filed Aug. 19, 2009, the entire contents of which are hereby incorporated by reference herein and are made a part of this specification. The features of the vial access devices as described herein may also be combined with any of the features of the embodiments described in U.S. patent application Ser. No. 14/307,320, titled "PRESSURE-REGULATING VIAL ADAPTORS AND METHODS", filed Jun. 17, 2014, the entire contents of which are hereby incorporated by reference herein and are made a part of this specification.

The vial access devices described herein may include any kind of system, assembly, device, or component that may be used to access the contents of a container in a pressure-regulating manner. Some non-limiting examples of vial access devices include vial adaptors and syringe adaptors. In order to facilitate easier understanding, the figures herein are described with regards to a vial adaptor. However, any of the features or combinations of features may be applied to other types of vial access devices.

The container may be any type of container capable of storing liquid and/or gas. In general, the container may be hermetically sealed to preserve the contents of the container in a sterile environment. The container may be evacuated or pressurized upon sealing. In some instances, the container may be partially or completely filled with a liquid, such as a drug or other medical fluid. In such instances, one or more gases may also be sealed in the container.

When coupled to the container, the vial access device may generally provide access to the contents of the container such that the contents may be removed or added to. In some configurations, the vial access device comprises an extractor which provides the access to the contents of the container by providing fluid communication between the interior and exterior of the container once the device is coupled to the container. In some configurations, the extractor may comprise an extractor channel or a passageway between the interior and exterior of the container when the device is coupled to the container.

In some configurations, the extractor may only allow fluid communication between the interior and exterior of the container when the device is coupled to the container and the adaptor is in a specific mode or physical configuration. For example, the device may have one mode or physical configuration in which the extractor is closed or obstructed, such that, if the device were coupled to the container there would not be fluid communication between the interior and exterior of the container. That device may have an alternate mode or physical configuration in which the extractor is open or no longer obstructed, such that, if the device were coupled to the container there would be fluid communication between the interior and exterior of the container. In some configurations, a user may be able to selectively place the device into a specific mode or physical configuration that allows for fluid communication between the interior and exterior of the container via the extractor when the device is coupled with the container.

When coupled to the container, the device may have certain features that allow for the removal of all of the contents of the container without a significant change in pressure within the container. In some configurations, the device comprises a regulator which allows for a substantially constant pressure within the container when the device is coupled to the container.

In some configurations, the regulator regulates the pressure within the container. As used herein, the term regulate, or any derivative thereof, is a broad term used in its ordinary sense and includes, unless otherwise noted, any active, affirmative, or positive activity, or any passive, reactive, respondent, accommodating, or compensating activity that tends to effect a change. In some configurations, the regulator substantially maintains a pressure difference, or equilibrium, between the interior of the container and the surrounding environment. As used herein, the term maintain, or any derivative thereof, is a broad term used in its ordinary sense and includes the tendency to preserve an original condition for some period, whether or not that condition is ultimately altered. In some instances, the regulator maintains a substantially constant pressure within the container. In certain instances, the pressure within the container varies by no more than about 1 psi, no more than about 2 psi, no more than about 3 psi, no more than about 4 psi, or no more than about 5 psi.

In some instances, the regulator equalizes pressures exerted on the contents of the container. As used herein, the term equalize, or any derivative thereof, is a broad term used in its ordinary sense and includes the movement toward equilibrium, whether or not equilibrium is achieved. In certain of such instances, the regulator may maintain a stable pressure within the container by allowing or encouraging equalization of a pressure difference between the interior and exterior of the container. For example, the regulator may allow the equalization of a pressure difference between the interior of the container and the ambient air surrounding the container, or the regulator may allow equalization of a pressure difference between the interior of the container and an environment within an exchange device.

Thus, coupling the device to the container may allow for the removal of all of the contents of the container via the extractor while the regulator maintains a stable pressure within the container by allowing any pressure difference between the interior and exterior of the container to be equalized. In some arrangements, a single device comprises the regulator and the extractor, while in other arrangements, the regulator and the extractor are separate units.

In some configurations, the regulator may only maintain a stable pressure within the container when the device is coupled to the container and the device is in a specific mode or physical configuration. For example, the device may have one mode or physical configuration in which the regulator is closed or obstructed, such that, if the device were coupled to the container any pressure difference would not be equalized. That device may have an alternate mode or physical configuration in which the regulator is open or no longer obstructed, such that, if the device were coupled to the container there would be equalization of any pressure difference. In some configurations, a user may be able to selectively place the device into a specific mode or physical configuration that allows for the regulator to equalize any pressure difference between the interior and exterior of the container when the device is coupled with the container.

In some embodiments, the regulator provides fluid communication between the interior or exterior of the container and a reservoir. In certain of such configurations, the regulator may comprise a regulator channel or a passageway in fluid communication between a reservoir and either the interior or exterior of the container when the device is coupled to the container.

In some embodiments, the reservoir may be the ambient air outside the container. However, in other embodiments, the reservoir may be any rigid or semi-rigid structure that can hold a volume of gas in order for a substantially constant pressure to be maintained within the container. As used herein, the term reservoir may include, without limitation, any sack, bag, balloon, bladder, container, receptacle, regulating enclosure, diaphragm, or membrane. The reservoir may be capable of expanding, contracting, and/or folding, and may include structures comprising a flexible, supple, pliable, resilient, elastic, and/or expandable material. For example, the reservoir may be a closed bag configured to expand or contract either outside or within the container in order to maintain a substantially constant pressure within the container. In some configurations, the reservoir comprises at least a portion of the environment surrounding the container. In some configurations, the reservoir comprises a container, canister, bag, or other holder dedicated to the adaptor. In some embodiments, the reservoir comprises a gas and/or a liquid. It may be preferable that the reservoir comprise mainly gas so as not to dilute any liquid contents of the container.

In some configurations, the extractor may be coupled to an exchange device. In certain instances, the extractor and the exchange device are separable. In some instances, the extractor and the exchange device are integrally formed. The exchange device is configured to accept fluids and/or gases from the container via the extractor, to introduce fluids and/or gases to the container via the extractor, or to do some combination of the two. In some arrangements, the exchange device is in fluid communication with the extractor. In some configurations, the exchange device comprises a medical instrument, such as a syringe. In some instances, the exchange device is configured to remove some or all of the contents of the container via the extractor. In certain arrangements, the exchange device can remove the contents independent of pressure differences, or lack thereof, between the interior of the container and the surrounding environment. For example, in instances where the pressure outside of the container exceeds that within the container, an exchange device comprising a syringe can remove the contents of the container if sufficient force is exerted to extract the plunger from the syringe. The exchange device can similarly introduce fluids and/or gases to the container independent of pressure differences between the interior of the container and the surrounding environment.

It should be noted that this disclosure makes frequent reference to example embodiments of vial adaptors and vials, such as medicinal vials typically used to store and transport medicine, in order to facilitate an easier understanding of the concepts described herein. The descriptions regarding the vials and vial adaptors are not intended to be limiting and may be applied to any container and any vial access device configured to be coupled to that container. Although embodiments and examples are provided herein in the medical field, the inventions are not confined to the medical field only and certain embodiments can be used in many other fields.

Numerous medicines and other therapeutic fluids are stored and distributed in medicinal vials of various shapes and sizes. Often, these vials are hermetically sealed to prevent contamination or leaking of the stored fluid. The pressure differences between the interior of the sealed vials and the particular atmospheric pressure in which the fluid is later removed often give rise to various problems.

For instance, introducing the piercing member of a vial adaptor through the septum of a vial can cause the pressure within the vial to rise sharply. This pressure increase can cause fluid to leak from the vial at the interface of the septum and piercing member or at the attachment interface of the adaptor and a medical device, such as a syringe. Also, it can be difficult to withdraw an accurate amount of fluid from a sealed vial using an empty syringe, or other medical instrument, because the fluid may be naturally urged back into the vial once the syringe plunger is released. As the syringe is decoupled from the vial, pressure differences can often cause a small amount of fluid to spurt from either the syringe or the vial. Additionally, in many instances, air bubbles are drawn into the syringe as fluid is withdrawn from the vial. To rid a syringe of bubbles after removal from the vial, medical professionals often flick the syringe, gathering all bubbles near the opening of the syringe, and then force the bubbles out. In so doing, a small amount of liquid usually is expelled from the syringe as well. Medical personnel generally do not take the extra step to re-couple the syringe with the vial before expelling the bubbles and fluid. In some instances, this may even be prohibited by laws and regulations. Such laws and regulations may also necessitate expelling overdrawn fluid at some location outside of the vial in certain cases. Moreover, even if extra air or fluid were attempted to be reinserted in the vial, pressure differences can sometimes lead to inaccurate measurements of withdrawn fluid.

To address these problems caused by pressure differentials, medical professionals frequently pre-fill an empty syringe with a precise volume of ambient air corresponding to the volume of fluid that they intend to withdraw from the vial. The medical professionals then pierce the vial and expel this ambient air into the vial, temporarily increasing the pressure within the vial. When the desired volume of fluid is later withdrawn, the pressure differential between the interior of the syringe and the interior of the vial is generally near equilibrium. Small adjustments of the fluid volume within the syringe can then be made to remove air bubbles without resulting in a demonstrable pressure differential between the vial and the syringe. However, a significant disadvantage to this approach is that ambient air, especially in a hospital setting, may contain various airborne viruses, bacteria, dust, spores, molds, and other unsanitary and harmful debris. The pre-filled ambient air in the syringe may contain one or more of these harmful substances, which may then mix with the medicine or other therapeutic fluid in the vial. If this contaminated fluid is injected directly into a patient's bloodstream, it can be particularly dangerous because it circumvents many of the body's natural defenses to airborne pathogens. Moreover, patients who need the medicine and other therapeutic fluids are more likely to be suffering from a diminished infection-fighting capacity.

In the context of oncology and certain other drugs, all of the foregoing problems can be especially serious. Such drugs, although helpful when injected into the bloodstream of a patient, can be extremely harmful if inhaled or touched. Accordingly, such drugs can be dangerous if allowed to spurt unpredictably from a vial due to pressure differences. These drugs are often volatile and may instantly aerosolize when exposed to ambient air. Accordingly, expelling a small amount of such drugs in order to clear a syringe of bubbles or excess fluid, even in a controlled manner, is generally not a viable option, especially for medical personnel who may repeat such activities numerous times each day. Consequently, there is a need for a vial adaptor that reduces the above-noted problems.

Certain devices exist that allow air to be drawn into a vial as fluid is removed therefrom. These devices generally use filters. Although filters remove a large number of contaminants from air as it enters the vial, the filters are not perfect. In some instances the filters are hydrophobic membranes comprising Gortex® or Teflon®. Multiple problems arise from such assemblies. For example, the hydrophobic nature of the filters prevents a user from returning overdrawn fluid to the vial. For example, in some instances, air is allowed into the vial through a channel as the user withdraws fluid from the vial. However, if the user forces fluid back into the vial, fluid is also forced through the channel until it contacts the filter. Because the filter is a barrier to fluid, the pressure within the vial will increase as the medical professional continues to force fluid into the vial. As stated above, such pressure increases are prohibited by law in some instances, and in any event, can make it difficult for the user to obtain an accurate dosage. In addition, pressure differences can easily damage the thin and delicate membranes, causing the filters to occasionally leak and permit harmful liquids to escape.

The use of Gortex® or Teflon® membranes in filters generally requires ethylene oxide (EtO) sterilization, which is expensive and inconvenient for medical device manufacturers. Preferred alternative methods of sterilization, such as gamma sterilization and electron beam sterilization, generally ruin such filters. In some instances, the latter forms of sterilization degrade the Teflon® membranes, making the filters prone to leakage.

In addition, some existing devices are difficult or complicated to couple with a vial and can require multiple specialized apparatuses to effectuate such coupling. Complicated procedures can become overly burdensome to medical personnel who repeat the procedures numerous times each day. Certain such complicated devices are bulky and unbalanced. Coupling such a device with a vial generally creates a top-heavy, metastable system that is prone to being tipped over and possibly spilled.

In addition, some existing devices may be ineffective with certain vial shapes, sizes, or configurations. In some instances, the vial may have a reduced height, a narrow neck, a long neck, a thick septum, a nonstandard septum, and/or be narrow in diameter, which can make it difficult or complicated to couple vial access devices to the vial or fit components of the devices inside the vial. Furthermore, any pressure-regulating mechanisms in existing devices may not work properly with a vial that has a capacity less than or equal to about 50 mL, less than or equal to about 25 mL, less than or equal to about 15 mL, less than or equal to about 5 mL, and/or a vial neck diameter less than or equal to about 10.5 mm. Some embodiments provide a vial access device configured to work with one or more such vials identified in the preceding sentence.

At least some vial access device embodiments disclosed herein reduce or eliminate some or all of the above-noted problems.

FIG. 1 is a schematic illustration of a container 110, such as a medicinal vial, that can be coupled with an extractor 120 and a regulator 130. In certain arrangements, the regulator 130 allows the removal of some or all of the contents of the container 110 via the extractor 120 without a significant change of pressure within the container 110.

In general, the container 110 is hermetically sealed to preserve the contents of the container 110 in a sterile environment. The container 110 can be evacuated or pressurized upon sealing. In some instances, the container 110 is partially or completely filled with a liquid, such as a drug or other medical fluid. In such instances, one or more gases can also be sealed in the container 110. Although embodiments and examples are provided herein in the medical field, the inventions are not confined to the medical field only and certain embodiments can be used in many other fields.

The extractor 120 generally provides access to contents of the container 110 such that the contents may be removed or added to. In certain arrangements, the extractor 120 comprises an opening between the interior and exterior of the container 110. The extractor 120 can further comprise a passageway between the interior and exterior of the container 110. In some configurations, the passageway of the extractor 120 can be selectively opened and closed. In some arrangements, the extractor 120 comprises a conduit extending through a surface of the container 110. The extractor 120 can be introduced to the container 110 after the container 110 has been sealed. In certain embodiments, the extractor 120, or some portion thereof, is located within the container 110 when coupled with the container 110.

In some configurations, the extractor 120 is in fluid communication with the container 110, as indicated by an arrow 21. In certain of these configurations, when the pressure inside the container 110 varies from that of the surrounding environment, the introduction of the extractor 120 to the container 110 causes a transfer through the extractor 120. For example, in some arrangements, the pressure of the environment that surrounds the container 110 exceeds the pressure within the container 110, which may cause ambient air from the environment to ingress through the extractor 120 upon insertion of the extractor 120 into the container 110. In other arrangements, the pressure inside the container 110 exceeds that of the surrounding environment, causing the contents of the container 110 to egress through the extractor 120.

In some instances, the exchange device 140 is configured to remove some or all of the contents of the container 110 via the extractor 120. In certain arrangements, the exchange device 140 can remove the contents independent of pressure differences, or lack thereof, between the interior of the container 110 and the surrounding environment. For example, in instances where the pressure outside of the container 110 exceeds that within the container 110, an exchange device 140 comprising a syringe can remove the contents of the container 110 if sufficient force is exerted to extract the plunger from the syringe. The exchange device 140 can similarly introduce fluids and/or gases to the container 110 independent of pressure differences between the interior of the container 110 and the surrounding environment.

In certain configurations, the regulator 130 is coupled with the container 110. The regulator 130 generally regulates the pressure within the container 110. As used herein, the term regulate, or any derivative thereof, is a broad term used in its ordinary sense and includes, unless otherwise noted, any active, affirmative, or positive activity, or any passive, reactive, respondent, accommodating, or compensating activity that tends to effect a change. In some instances, the regulator 130 substantially maintains a pressure difference, or equilibrium, between the interior of the container 110 and the surrounding environment. As used herein, the term maintain, or any derivative thereof, is a broad term used in its ordinary sense and includes the tendency to preserve an original condition for some period, whether or not that condition is ultimately altered. In some instances, the regulator 130 maintains a substantially constant pressure within the container 110. In certain instances, the pressure within the container 110 varies by no more than about 1 psi, no more than about 2 psi, no more than about 3 psi, no more than about 4 psi, or no more than about 5 psi. In still further instances, the regulator 130 equalizes pressures exerted on the contents of the container 110. As used herein, the term equalize, or any derivative thereof, is a broad term used in its ordinary sense and includes the movement toward equilibrium, whether or not equilibrium is achieved. In other configurations, the regulator 130 is coupled with the container 110 to allow or encourage equalization of a pressure difference between the interior of the container 110 and some other environment, such as the environment surrounding the container 110 or an environment within the exchange device 140. In some arrangements, a single device comprises the regulator 130 and the extractor 120, while in other arrangements, the regulator 130 and the extractor 120 are separate units.

The regulator 130 is generally in communication with the container 110, as indicated by an arrow 31. The regulator 130 may also generally be in communication with a reservoir, such as the reservoir 150-*a*, as indicated by the arrow 35, or the reservoir 150-*b*, as indicated by the arrow 36. The reservoir 150-*a* is external to the container 110. In some configurations, the reservoir 150-*a* comprises at least a portion of the environment surrounding the container 10. The reservoir 150-*b* is at least partially internal to the container 110, and in some cases may be introduced to the container 110.

In some configurations, the reservoir (either the reservoir 150-*a* or 150-*b*) comprises a container, canister, bag, or other holder dedicated to the regulator 130. As used herein, the term bag is a broad term used in its ordinary sense and includes, without limitation, any sack, balloon, bladder, receptacle, reservoir, enclosure, diaphragm, or membrane capable of expanding and/or contracting, including structures comprising a flexible, supple, pliable, resilient, elastic, and/or expandable material. In some embodiments, the reservoir 150 comprises a gas and/or a liquid.

In certain embodiments, the regulator 130 provides fluid communication between the container 110 and the reservoir 150-*a* or 150-*b*. In certain of such embodiments, it is preferred that the reservoir 150-*a* or 150-*b* comprise mainly gas so as not to dilute any liquid contents of the container 10. In other embodiments, the regulator 130 prevents fluid communication between the container 110 and the reservoir 150-*a* or 150-*b*. In certain of such embodiments, the regulator 130 serves as an interface between the container 110 and the reservoir 150-*a* or 150-*b*. In some arrangements, the regulator 130 comprises a substantially impervious bag for accommodating ingress of gas and/or liquid to the container 110 or egress of gas and/or liquid from the container 110.

In some embodiments, the extractor 120, or some portion thereof, is located within the container 110. In some embodiments, the regulator 130, or some portion thereof, is located within the container 10. It is possible to have any combination of the extractor 120, or some portion thereof, entirely within, partially within, or outside of the container 110 and/or the regulator 130, or some portion thereof, entirely within, partially within, or outside of the container 110. The regulator 130 can be in fluid or non-fluid communication with the container 110. In some embodiments, the regulator 130 is located entirely within the container 110. In certain of such embodiments, the regulator 130 comprises a closed bag configured to expand or contract within the container 110 to maintain a substantially constant pressure within the container 110. In other embodiments, the regulator 130 is in communication, either fluid or non-fluid, with the reservoir 150-*a*, as indicated by the arrow 35, or with the reservoir 150-*b*, as indicated by the arrow 36.

Figure 2:
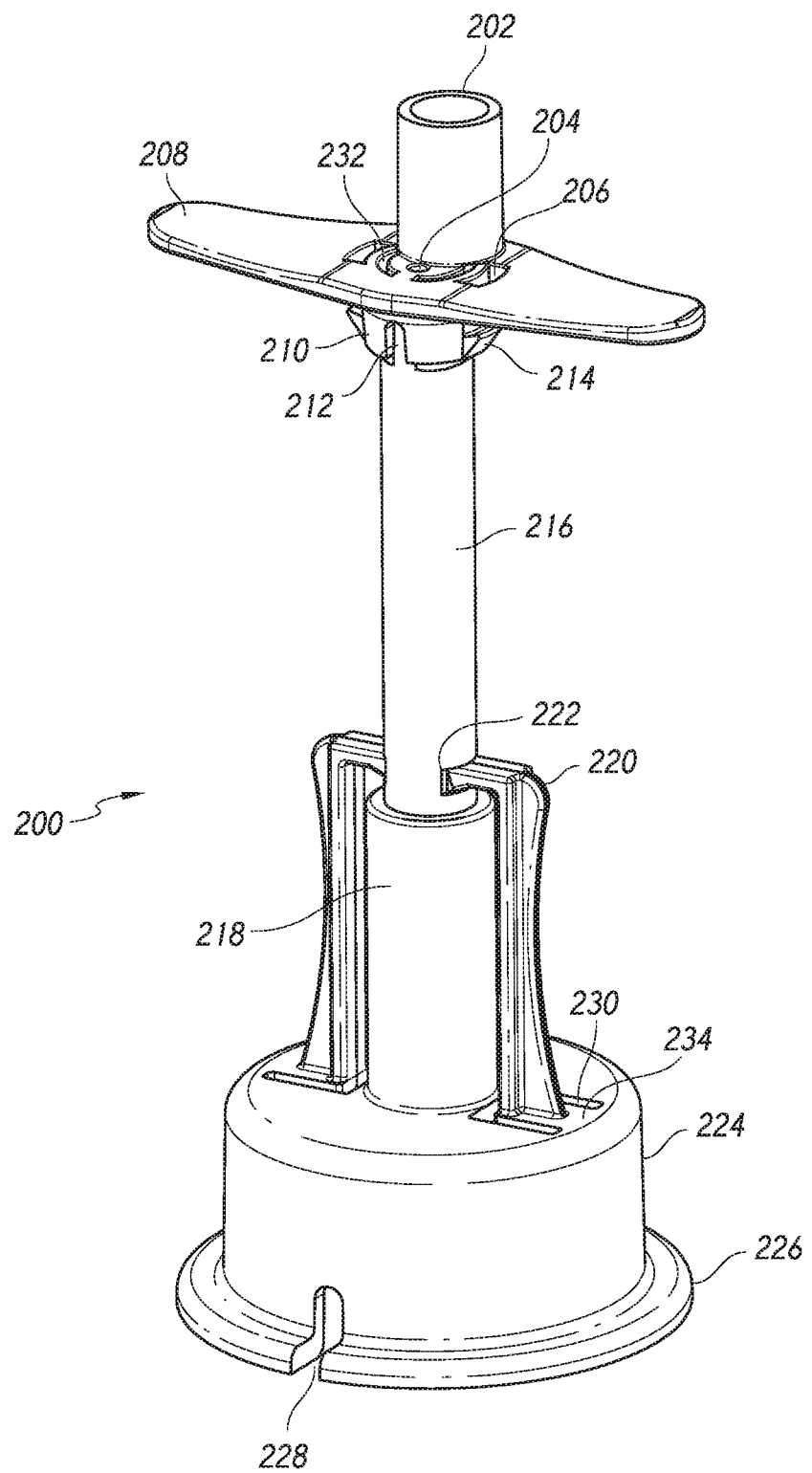
FIG. 2 is a perspective view of one embodiment of a vial adaptor in an initial stage.
Figure 3:
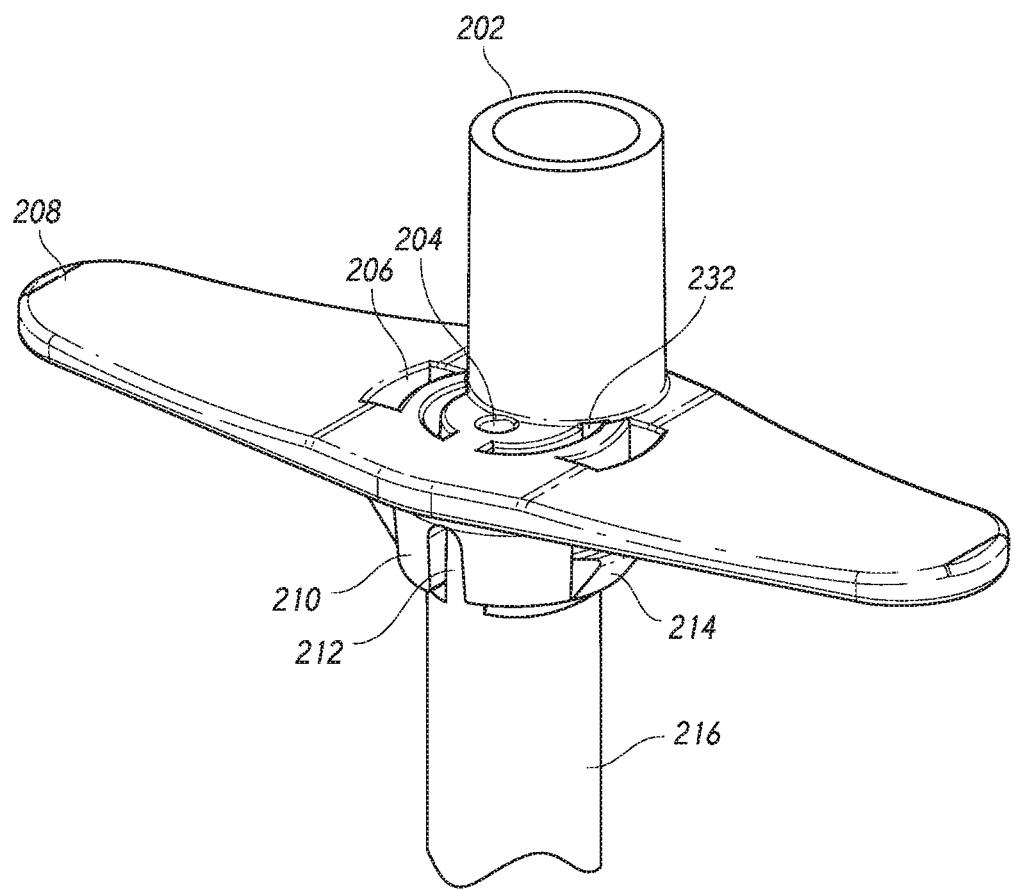
FIG. 3 is a partial perspective view of the proximal end of the vial adaptor shown in FIG. 2.
Figure 4:
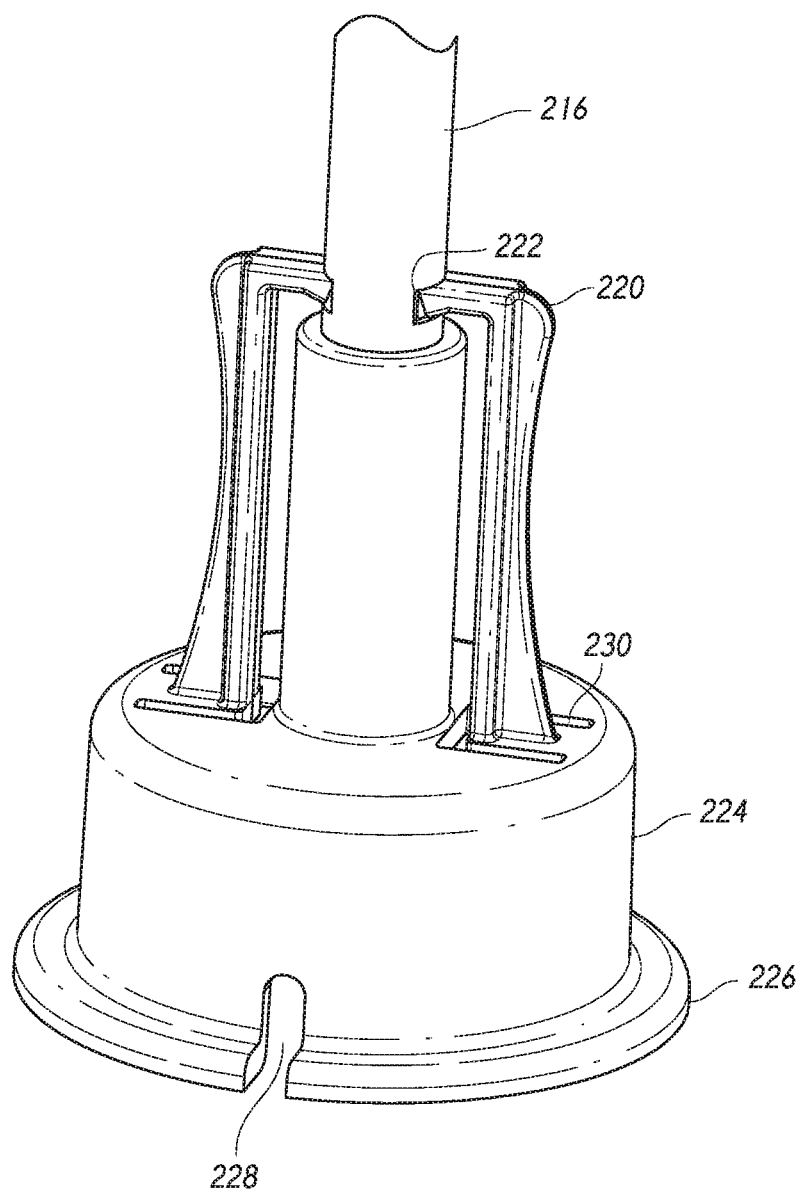
FIG. 4 is a partial perspective view of the distal end of the vial adaptor shown in FIG. 2.

FIG. 2 is a perspective view of an embodiment of a vial adaptor in an initial stage prior to coupling with a vial. FIG. 3 is a partial perspective view of the proximal end of the same vial adaptor shown in FIG. 2. FIG. 4 is a partial perspective view of the distal end of the vial adaptor shown in FIG. 2. For this reason, the features of the adaptor 200 shown in FIGS. 2-4 are described together in the following paragraphs.

As used herein, the term "proximal" may refer to a direction of the adaptor that is typically pointed towards a user (e.g., the direction of the medical connector interface), whereas the term "distal" may refer to a direction of the adaptor that is typically pointed away from the user (e.g., towards the direction of the piercing member or where the adaptor engages the vial). The "proximal end" of the adaptor or any component in the adaptor may include a terminal end towards the proximal direction, and may also include a proximal section or portion surrounding the terminal end, such as, for example, a section of a component extending a certain distance from the terminal end, where the distance can be an absolute distance (such as, for example, less than or equal to about 1 mm, less than or equal to about 5 mm, less than or equal to about 10 mm, or less than or equal to about 20 mm from the terminal end) or a portion of an elongate dimension of the component (such as, for example, within 10% of the elongate dimension, within 25% of the elongate dimension, or within 50% of the elongate dimension from the terminal end). Likewise, the "distal end" of the adaptor or any component may include a terminal end towards the distal direction, and may also include some distal section or portion surrounding the proximal end, similar to the section or portion as defined with respect to the proximal end. For example, if the adaptor is divided lengthwise into two halves, a proximal half and a distal half, it is conceivable that the "proximal end" may include any section or portion of the proximal half up to its terminal end. In some cases, the entire proximal half may be referred to as the proximal end.

In some embodiments, an adaptor 200 may comprise an insertion member 216 and an insertion member channel 218. In some configurations, the insertion member 216 is a sliding insertion member 216. The insertion member channel 218 may be substantially hollow, defining a chamber (not shown) through which the insertion member 216 may slide through to move axially. The insertion member 216 may also comprise a piercing member (not shown) at the distal end of the insertion member 216. The piercing member is described in further detail in regards to FIG. 5. Moving the insertion member 216 in an axial direction may also move the piercing member in that same direction.

In some configurations, the insertion member 216 and the piercing member may be a single unit and integrally formed of a unitary piece of material. Thus, any description or reference to a piercing member in this disclosure may be applicable to the insertion member 216, and any description or reference to the insertion member 216 may be applicable to the piercing member. In other configurations, the insertion member 216 and the piercing member may be distinct units that are mechanically coupled in substantially airtight engagement. For example, the insertion member 216 may be adhered to the proximal base of a piercing member. In some instances they are adhered to each other by glue, epoxy, ultrasonic welding, or secured/joined in threaded, snapped, or friction-fit engagement. Other methods of attachment are also possible.

In some embodiments, the insertion member 216 and the piercing member may define a regulator channel and/or an extractor channel. In some embodiments, only the insertion member 216 may comprise a regulator channel and/or an extractor channel, while in yet other embodiments, only the piercing member may comprise a regulator channel and/or extractor channel. The regulator channel and the extractor channel are described in further detail in regards to FIG. 5 and FIG. 11.

In various configurations, the insertion member 216 may fully or partially reside in the insertion member channel 218, or the insertion member 216 may not reside in the insertion member channel 218 at all. In the illustration, the insertion member 216 partially resides in the insertion member channel 218 and the shaft of the insertion member 216 is visible.

In some embodiments, the adaptor 200 or a similar vial access device is configured to connect to the vial. However, in certain embodiments, the adaptor 200 comprises a cap connector 224, which may be used to connect to the vial. The cap connector 224 may be shaped in a way that substantially conforms to the shape of a cap of a container, such that the adaptor 200 may be coupled to that container. As illustrated, the cap connector 224 has a shape that substantially conforms to the shape of a cap of a vial, which can be seen in further detail in regards to FIG. 6. In some embodiments, the cap connector 224 resembles the structures shown in FIGS. 7 and 8 of, and described in, the specification of U.S. Pat. No. 5,685,866, titled "MEDICAL VALVE AND METHOD OF USE", filed on Nov. 4, 1994, the entire contents of which are hereby incorporated by reference herein and are made a part of this specification.

In certain configurations, the cap connector 224 comprises a rigid material, such as plastic or metal that substantially maintains its shape after minor deformations. In some embodiments, the cap connector 224 comprises polycarbonate plastic. In some arrangements, the cap connector 224 is configured to tightly engage with the cap of a vial. For example, the cap connector 224 may be configured to snap over a feature of the vial, such as a ridge, lip, or neck of the vial. In some instances, the cap connector 224 may comprise a material around an interior surface for forming a substantially airtight seal with the cap of a vial. In some embodiments, the cap connector 224 comprises an elastic material that is stretched over a feature of the vial in order to form a seal around the cap of the vial. In some embodiments, the cap connector 224 comprises one or more projections for securing the adaptor 200 to the cap of the vial. The projections are described in further detail in regards to FIG. 5, and an illustrative example of how the cap connector 224 may tightly engage the cap of a vial can be seen by comparing FIG. 6 and FIG. 7.

In some embodiments, the cap connector 224 is sized and configured such that an inner surface of the cap connector 224 contacts the cap of the vial. In some embodiments, a portion of the cap connector 224 contacts the cap in substantially airtight engagement. In certain embodiments, a portion of the inner surface of the cap connector 224 that would surround either the septum or casing of the vial is lined with a material, such as rubber or plastic, to ensure the formation of a substantially airtight seal between the adaptor 200 and the vial. More information about seals within the cap connector 224 is provided in further detail in regards to FIG. 5. In some embodiments, the cap connector 224 may comprise a base having a plane where the cap connector 224 touches the cap of a vial. Accordingly, in some embodiments, the adaptor 200 may be connected to the vial through the use of the cap connector 224, while in other embodiments, the adaptor 200 may connect to the vial through another method. For example, the adaptor 200 may engage the vial through the use of adhesive, tape, or any other means. In some embodiments, the adaptor 200 may have a vial engagement assembly that allows the adaptor 200 to engage the vial in the same direction as the insertion member 216 (e.g., the direction that the insertion member 216 slides towards) or the piercing member. In some of such embodiments, the vial engagement assembly may use adhesive, tape, or other means of coupling the vial to the adaptor 200.

In some configurations, the cap connector 224 comprises a skirt configured to encircle a portion of the vial. In some embodiments, the skirt may extend around less than the entire circumference of the vial. For example, the cap connector 224 may comprise a recess 228 as shown in FIG. 2. In other embodiments, the recess 228 may be a notch or a longitudinal slit. More information regarding the role of the recess 228 is provided in regards to FIG. 12. Advantageously, the skirt may extend distally beyond the tip of the piercing member. This configuration partially shields the tip from users prior to insertion of the piercing member into the vial, thereby helping to prevent accidental contact with the tip. The skirt may further provide a coupled adaptor 200 and a vial with a lower center of mass, thereby making the coupled items less likely to tip over.

In some configurations, the cap connector 224 comprises a lip 226. The lip 226 further provides a coupled adaptor 200 and a vial with a lower center of mass, thereby making the coupled items less likely to tip over. The lip 226 may also provide leverage to make it easier for a user to couple or uncouple the adaptor 200 with a vial. For example, it may be easier to couple the adaptor 200 and the vial when a user pushes down on the lip 226 to slide the cap connector 224 over the cap of the vial, as opposed to the user grasping the cap connector 224 on its sides. The user may similarly grasp the lip 226 in order to uncouple the adaptor 200 from the vial. In some configurations, grasping the lip 226 makes it easier to uncouple the adaptor 200 from the vial by unseating or reorienting the projections of the cap connector 224, which reduces their grip on the vial.

In some configurations, the cap connector 224 comprises the insertion member channel 218. In some arrangements, the cap connector 224 and the insertion member channel 218 are integrally formed of a unitary piece of material. In other arrangements, the cap connector 224 and the insertion member channel 218 are separate units in substantially airtight engagement. In some arrangements, the cap connector 224 comprises polycarbonate plastic.

In some embodiments, the insertion member 216 and any other components attached thereto (e.g., a piercing member, the locking ring 210, the handle 208, and so forth) may be part of an insertion assembly. In some embodiments, any components which are not part of the insertion assembly may be part of a housing (e.g., the cap connector 224, the insertion member channel 218, the engagement members 220, and so forth). The housing may define an insertion path, through which the insertion assembly slides.

In certain embodiments, the adaptor 200 may have multiple modes or physical configurations. The adaptor 200 may be able to transition between the different modes or physical configurations, and in some such cases the adaptor 200 may be able to transition between the different modes or physical configurations after it has been coupled to a vial or while the adaptor 200 is being coupled to a vial. In some arrangements, a user may be able to selectively switch or transition the adaptor 200 between different modes or physical configurations.

In certain embodiments, the adaptor 200 may have one mode or physical configuration in which the interior and exterior of the vial would not be fluid communication with each other while the adaptor 200 is coupled to the vial. For example, in such a mode or physical configuration the extractor channel may be closed or obstructed. In certain embodiments, the adaptor 200 may have one mode or physical configuration in which any pressure difference between the interior and the exterior of the vial would not be equalized while the adaptor 200 is coupled to the vial. For example, the regulator channel may be closed or obstructed, any reservoir may be inaccessible or not yet deployed, and so forth. The modes or physical configurations in which no fluid communication or pressure equalization occurs between the interior and the exterior of the vial may be a single mode or physical configuration, or they may be separate modes and physical configurations.

In certain embodiments, the adaptor 200 may have one mode or physical configuration in which the interior and exterior of the vial are in fluid communication with each other while the adaptor 200 is coupled to the vial. For example, in such a mode or physical configuration the extractor channel may be open or unobstructed. In certain embodiments, the adaptor 200 may have one mode or physical configuration in which any pressure difference between the interior and the exterior of the vial is equalized while the adaptor 200 is coupled to the vial. For example, the regulator channel may be open or unobstructed, or the reservoir may be accessible or deployed, and so forth. The modes or physical configurations in which fluid communication or pressure equalization may occur between the interior and the exterior of the vial may be a single mode or physical configuration, or they may be separate modes and physical configurations.

In some configurations, the adaptor 200 may have features that hold the adaptor 200 in a specific mode or physical configuration until it is ready to be transitioned into a different mode or physical configuration. In some configurations, the adaptor 200 may comprise a mode selecting assembly or a physical configuration selecting assembly configured to keep the adaptor 200 in a specific mode or physical configuration. In some configurations, the adaptor 200 may have a locking mechanism or functionality that keep the adaptor 200 in a specific mode or physical configuration.

In some configurations, the adaptor 200 may have an initial stage and a subsequent stage. The adaptor 200 may have features which, in the initial stage of the adaptor 200, prevent the insertion member 216 and/or the piercing member from piercing the septum of the vial when the adaptor 200 is coupled to the vial. The adaptor 200 may have features that permit the insertion member 216 and/or the piercing member to be inserted into the vial only when the adaptor 200 is fully coupled to the vial. The adaptor 200 may also have features that prevent the insertion member 216 and/or the piercing member to be inserted into the vial at an angle. In some configurations, inserting the insertion member 216 and/or the piercing member into the vial may transition the adaptor 200 from its initial stage into its subsequent stage. The adaptor 200 may have features that, once the insertion member 216 has been inserted into the vial, keep the insertion member in its inserted position.

By way of example, FIG. 2 illustrates an embodiment of the adaptor 200 maintained in an initial stage by an insertion member engagement assembly.

In some configurations, the adaptor 200 may comprise an insertion member engagement assembly. The insertion member engagement assembly may provide a movement mechanism permitting the insertion member 216 to be inserted, as well as a locking functionality that maintains the insertion member 216 in either the un-inserted or inserted position. In some configurations, the insertion member engagement assembly may engage various portions of the insertion member 216 in order to maintain the adaptor 200 in its current stage. In some configurations, the insertion member engagement assembly may operate using a locking mechanism, such that the engagement of the insertion member engagement assembly with certain corresponding features of the insertion member 216 will lock the movement of both relative to one another. When the insertion member engagement assembly is not securely engaged to the insertion member 216, the insertion member 216 may be able to move axially. For example, the insertion member 216 may be free to move downwards towards a coupled vial, such that the portion of the insertion member 216 that is outwardly visible in the illustration may slide into the insertion member channel 218.

In some embodiments, the insertion member engagement assembly may hold the insertion member 216 or similar insertion assembly in place when the insertion member 216 is in a fully inserted position. In some embodiments, the insertion member engagement assembly may securely hold the insertion member 216 in place when the insertion member 216 is in a fully inserted position. As used herein, the term "securely hold" may mean that the insertion member engagement assembly maintains the insertion member 216 in the fully inserted position (e.g., the insertion member 216 would not retract if the adaptor 200 was turned upside down), and that it would be difficult to retract the insertion member 216 from the fully inserted position without substantial effort exerted by the user (e.g., the user may have to use two hands and pull at the insertion member 216 with enough force to subject the insertion member engagement assembly, or another component of the device, to a risk of breaking or mechanical failure).

In some configurations, the cap connector 224 comprises the insertion member engagement assembly. In some configurations, the insertion member engagement assembly comprises a pair of engagement members 220. However, in other configurations the insertion member assembly may comprise any number of engagement members 220.

In some configurations, the cap connector 224 may comprise an engagement member unlock 230. The engagement member unlock 230 may be any feature that allows the engagement members 220 to be unlocked or unengaged from the insertion member 216 in certain scenarios, which allows for the adaptor 200 to be transitioned between the initial stage and the subsequent stage. As shown in FIG. 1, the engagement member unlock 230 results from joining the base of each engagement member 220 at a location on the cap connector 224 that is partially surrounded by an opening in the cap connector 224. Thus, the base of each engagement member 220 is connected to the cap connector 224 at a location that may be flexible. In some configurations, the engagement member unlock 230 may be configured to re-position or flex outwards when the adaptor 200 is fully coupled to the vial, which may re-position the engagement members 220 so that they are no longer engaged with the insertion member 216 and allowing for insertion member 216 to move axially. In some configurations, the engagement members 220 are flexed outwards to disengage the insertion member 216. In some of such configurations, the engagement members 220 may flex out easily. Thus, the insertion member engagement assembly and the engagement member unlock 230 may prevent angled insertion of the insertion member 216 into a vial by allowing the insertion member 216 to be inserted only when the adaptor 200 is fully coupled to the vial and the insertion member 216 is perpendicular to the septum of the vial. In some embodiments, when the adaptor 200 is fully coupled to the vial the insertion member 216 may abut or partially pierce the septum of the vial prior to insertion of the insertion member 216. The mechanism of the engagement member unlock 230 is further described in regards to FIG. 7.

In some configurations, the structure pivots 234 may allow the engagement members 220 to be unlocked or unengaged from the insertion member 216 in certain scenarios, so that the adaptor 200 can be transitioned between the initial stage and the subsequent stage. The base of each engagement member 220 may be connected to one side of a structure pivot 234. In some embodiments, each structure pivot 234 may be defined by an opening in the cap connector 224. In the figure, each structure pivot 234 is associated with an opening that defines three sides of that structure pivot 234, such that each structure pivot 234 has one side that serves as the connection point between that structure pivot 234 and the cap connector 224. This allows the structure pivot 234 to pivot along the axis defined by that connection point. For example, a structure pivot 234 may be able to pivot upwards to allow the attached engagement member 220 to flex upwards and outwards. Thus, when the adaptor 200 is fully coupled to the vial, the vial would push all of the structure pivots 234 to flex upwards, which would also make the engagement members 220 flex upwards and outwards so that they are no longer engaged with the insertion member 216.

In some configurations, the insertion member 216 may comprise a pair of notches 222 configured to engage the engagement members 220 and maintain the adaptor 200 in its initial stage. However, in other configurations the insertion member 216 may comprise any number of notches 222, although generally the number of notches 222 will match the number of engagement members 220. As seen in FIG. 2, the engagement members 220 comprise arms that are securely engaged with the notches 222 in the insertion member 216, which prevent the insertion member 216 from moving axially when the adaptor 200 is in its initial stage. Thus, the insertion member 216 cannot be slid downwards further into insertion member channel 218 until the adaptor 200 is coupled to the vial and each engagement member unlock 230 is flexed outwards. As a result, the adaptor 200 cannot freely transition from its initial stage to its subsequent stage when the engagement members 220 are securely engaged with the notches 222.

In some configurations, the insertion member 216 may also comprise a locking ring 210, which may be integrally formed with the insertion member 216 or it may be a separate unit. In some configurations, the locking ring 210 may comprise a recess 212 that creates a pivot point for the locking ring 210 when the locking ring 210 is attached to the insertion member 216. In some configurations, the locking ring 210 may comprise a pair of tabs 214. However, in other configurations, the locking ring 210 may comprise any number of tabs 214, although generally the number of tabs 214 will match the number of engagement members 220. In still other configurations, the locking ring 210 may comprise tabs 214 that substantially surround the insertion member 216, preventing the engagement members 220 from releasing the tabs 214 upon rotation of the insertion member 216. The tabs 214 may be configured to be engaged with the engagement members 220 in order to maintain the adaptor 200 in its subsequent stage. In some configurations, the recess 212 is configured to engage with a protrusion (not shown) on the proximal end of the insertion member channel 218 when the adaptor 200 is in its subsequent stage, and that engagement may prevent, inhibit, or resist the insertion member 216 from rotating and/or flexing relative to the insertion member channel 218 when the insertion member 216 is fully inserted. This feature may be useful to prevent the engagement members 220 from slipping off the tabs 214 used to engage the engagement members 220 to the locking ring 210, since the tabs 214 do not wrap around the entire circumference of the locking ring 210. Otherwise, accidentally rotating the handle 208 may rotate the insertion member 216 to the point that the engagement members 220 are no longer secured to the locking ring 210. Additional features of the locking ring 210 are described further in regards to FIG. 10.

In some embodiments, an audible sound or report is produced when the insertion member 216 is pushed all the way in. In some of such embodiments, the sound is produced when the engagement members 220 engage with the locking ring 210. A solid, loud snap sound may be preferable over a weak or fait sound, since the sound may indicate to the user that the insertion member 216 is inserted all the way in and secured into place. Thus, the user may understand that hearing this sound may indicate that the adaptor 200 is ready for use in accessing or withdrawing the contents of the vial. This audible sound or report may play a similar role as the openings 206 that may also allow the user to quickly determine if the insertion member 216 is fully inserted and secured into place, and these features may be used in combination to create a redundant way for a user to determine if the adaptor 200 is ready to use.

In some embodiments, coupling the adaptor 200 to the vial while the adaptor 200 is in the initial stage does not puncture the vial. In some configurations, the position of the insertion member 216 during the initial stage, as shown in the illustration, causes the piercing member (not shown) to initially reside within the insertion member channel 218 and prevents the piercing member from entering the vial. Coupling the vial to the adaptor 200 may trigger the engagement member unlock 230 and disengages the arms of engagement members 220 from the notches 222 of the insertion member 216. This allows the insertion member 216 to move axially and to be slid further into the insertion member channel 218.

In some embodiments, the adaptor 200 comprises a handle 208. In some embodiments, the handle 208 is coupled to the proximal end of the insertion member 216. Once the engagement members 220 are disengaged, a user may be able to use the handle 208 to push the insertion member 216 downwards towards the coupled vial. As the insertion member 216 is slid further into insertion member channel 218, the piercing member that initially resided in the insertion member channel 218 may enter the vial. In some configurations, pushing in the insertion member 216 completely transitions the adaptor 200 from the initial stage, shown in the illustration, to a subsequent stage. Thus, the user may be able to use the handle 208 to push in the insertion member 216 and selectively transition the adaptor 200 from an initial stage to subsequent stage only upon coupling the adaptor 200 to a vial. During this transition from the initial stage to the subsequent stage, the piercing member pierces and enters the vial. This transition can be seen by comparing FIG. 7 and FIG. 8.

In some configurations, the subsequent stage may be a specific mode or physical configuration of the adaptor 200 that allows the adaptor 200 to add or withdraw fluid from the vial while a stable pressure is maintained within the vial. The features of the subsequent stage of the adaptor 200 are described in further detail in regards to FIGS. 9-13.

In some configurations, after the adaptor 200 enters its subsequent stage, the insertion member engagement assembly may keep the adaptor 200 in its subsequent stage and prevent the adaptor 200 from reverting to its initial stage. In some configurations, after the adaptor 200 enters its subsequent stage, the insertion member engagement assembly also prevents the insertion member 216 from moving axially or sliding back out of the vial. In the illustrated embodiment of FIG. 2, placing the adaptor 200 in its subsequent stage causes the engagement members 220 to be securely engaged with the tabs 214 of the locking ring 210. This locking feature can be seen by comparing FIG. 8 and FIG. 10.

In some configurations, the adaptor 200 may be configured such that it is impossible for a user to selectively transition the adaptor 200 from the subsequent stage back to its initial stage. In other configurations, it may be much more difficult for the user to transition the adaptor 200 from the subsequent stage to the initial stage than it is for a user to transition the adaptor 200 from the initial stage to the subsequent stage. In some configurations, it may be more difficult to disengage the engagement members 220 from the tabs 214 of the locking ring 210 than it is to disengage the engagement members 220 from the notches 222 of the insertion member 216. Such features may be desirable if the adaptor 200 is configured for single use, as they reduce the occurrence of leaks or spills by preventing a user from sliding the insertion member 216 back out of an unemptied vial.

In some configurations, the handle 208 may comprise one or more openings 206 and/or one or more openings 232. In some configurations, a user may be able to look through the openings 206 in order to check that the engagement members 220 are securely engaged with the tabs 214 of the locking ring 210. This conveniently provides a user more viewing angles to ensure a secure engagement instead of forcing the user to look between the handle 208 and the tabs 214. Since the adaptor 200 and a coupled vial may frequently be inverted while withdrawing the contents of the vial, a user may desire to ensure a secure engagement such that the adaptor 200 is in its subsequent stage. This may insure that the locking ring 210 is locked into place and that the insertion member 216 is prevented from moving axially. Otherwise, a leak or spill may occur while withdrawing the contents of the vial if the contents of the vial can exit through the space between the insertion member 216 and the insertion member channel 218, or if the insertion member 216 slides back out of the vial. In some embodiments, the engagement members 220 may be a different color from all the other components of the adaptor 200, or the engagement members 220 may just be a different color from the locking ring 210. By having the engagement members 220 be a different color from the locking ring 210, it reduces the time needed for a user to determine if the engagement members 220 are securely engaged with the locking ring 210 when looking through the openings 206. For example, if the user looks through the openings 206 and sees the color of the locking ring 210, it would indicate to the user that the engagement members 220 have not been securely engaged with the locking ring 210. This may suggest that the user needs to push in the insertion member 216 further until that secure engagement occurs. Alternatively, if the user looks through the openings 206 and sees the color of the engagement members 220, then it would mean the tabs 214 are no longer visible which indicates to the user that the engagement members 220 are securely engaged with the locking ring 210. Accordingly, the user can determine whether the adaptor 200 is ready and safe to use for accessing the contents of the vial based on the color observed through the openings 206, rather than having to make a closer examination of the contact between the engagement members 220 and the locking ring 210 or attempting to pull the insertion member 216 away from the vial (which may cause the contents of the vial to spill out). This color differentiation feature may also serve as a redundancy when used in combination with an audible sound or report created when the engagement members 220 are securely engaged to the locking ring 210.

In some embodiments, the openings 232 may play a role in assembling the adaptor, such as by allowing for an adhesive to be applied to a reservoir in order to attach the reservoir to the insertion member 216. Additional details regarding the role of the openings 232 are described further below in regards to methods of manufacturing.

The use of an insertion member engagement assembly comprising the engagement arms 220 is only an example of how the axial movement of the insertion member 216 and the locking ring 210 relative to the insertion member channel 218 may be restricted. Any other suitable means for locking the axial movement of the insertion member 216 and the locking ring 210 relative to the insertion member channel 218 may be employed. For example, the interior surface of the insertion member channel 218 and the exterior surface of the insertion member 216 may both comprise a series of corresponding beveled ridges. These ridges may be configured to allow the insertion member 216, with enough force applied, to slide downwards through the insertion member channel 218 without allowing the insertion member 216 to slide upwards through the insertion member channel 218. This would allow the insertion member 216 to remain outside the vial when the adaptor 200 is coupled to the vial, until the user pushes the insertion member 216 fully into the insertion member channel 218.

In certain embodiments, the adaptor 200 may comprise a medical connector interface 202 for coupling the adaptor 200 with a medical connector, another medical device, or any other exchange device or instrument used in extracting fluid from or injecting fluid into the vial (none of which are shown in the figure). In certain embodiments, the medical connector interface 202 may be connected to a proximal portion of an extractor channel (not shown) through which fluid may flow. In some instances, the extractor channel extends through the insertion member 216 such that the medical connector interface 202 may be in fluid communication with the interior of the vial when the adaptor 200 is coupled to the vial and the extractor channel is exposed to the contents of the vial. The extractor channel is described in further detail in regards to FIGS. 5 and 10, and the relationship between the medical connector interface 202 and the extractor channel is described in further detail in regards to FIG. 11. In some embodiments, the medical connector interface 202 may be used to connect to a syringe that is used to extract fluid from, or inject fluid into, the vial. In some of such embodiments, the medical connector interface 202 may be permanently attached to a syringe. The syringe may form a singular unit with the adaptor 200. In other of such embodiments, the syringe may be separable from the medical connector interface 202. The medical connector interface 202 may be able to accommodate connections with syringes of different sizes and dimensions, so that a user may connect varying syringes to the adaptor 200 based on the situation.

In certain embodiments, the medical connector interface 202 is not centered on an axial center of the adaptor 200. In some embodiments, the medical connector interface 202 is offset from an axial center of the extractor channel. However, in other embodiments, the medical connector interface 202 is centered on an axial center of the adaptor 200. Such a configuration may provide stability to a system comprising the adaptor 200 coupled with a vial, thereby making the coupled system less likely to tip over or cause dangerous leaks or spills occasioned by accidental bumping or tipping of the adaptor 200 or the vial.

In certain embodiments, the medical connector interface 202 may comprise a sidewall that may assume any suitable configuration for coupling with a medical connector, another medical device, or any other exchange device or instrument used in extracting fluid from or injecting fluid into the vial. In the illustrated embodiment, the sidewall is shown to be substantially cylindrical and located on the proximal end of the adaptor 200. In some embodiments, the sidewall may define a proximal portion of an extractor channel through which fluid may flow. In some embodiments, the thickness of the sidewall does not substantially vary at any given latitudinal cross-section of the medical connector interface 202.

In certain configurations, the medical connector interface 202 may comprise a flange (not shown) to aid in coupling the adaptor 200 with a medical connector, another medical device, or any other exchange device or instrument used in extracting fluid from or injecting fluid into the vial. The flange may be configured to accept any suitable medical connector, including connectors capable of sealing upon removal of a medical device therefrom. In some instances, the flange is sized and configured to accept the Clave® connector, available from ICU Medical, Inc. of San Clemente, Calif. Certain features of the Clave® connector are disclosed in U.S. Pat. No. 5,685,866, which was previously incorporated by reference. Connectors of many other varieties, including other needle-less connectors, can also be used. The connector can be permanently or separatably attached to the medical connector interface 202. In some arrangements, the flange may be threaded, configured to accept a Luer connector, or otherwise shaped to attach directly to a medical device, such as a syringe, or to other instruments.

In certain embodiments, the adaptor 200 comprises a regulator aperture 204. In many embodiments, the regulator aperture 204 is located at a position on the adaptor 200 that remains exposed to the exterior of the vial when the insertion member 216 is inserted in the vial. In the illustrated embodiment, the regulator aperture 204 is located in the handle 208 at the proximal end of the insertion member 216. In certain embodiments, the regulator aperture 204 allows fluid communication between the environment surrounding the vial and a regulator channel which extends through a portion of the insertion member 216.

Figure 5:
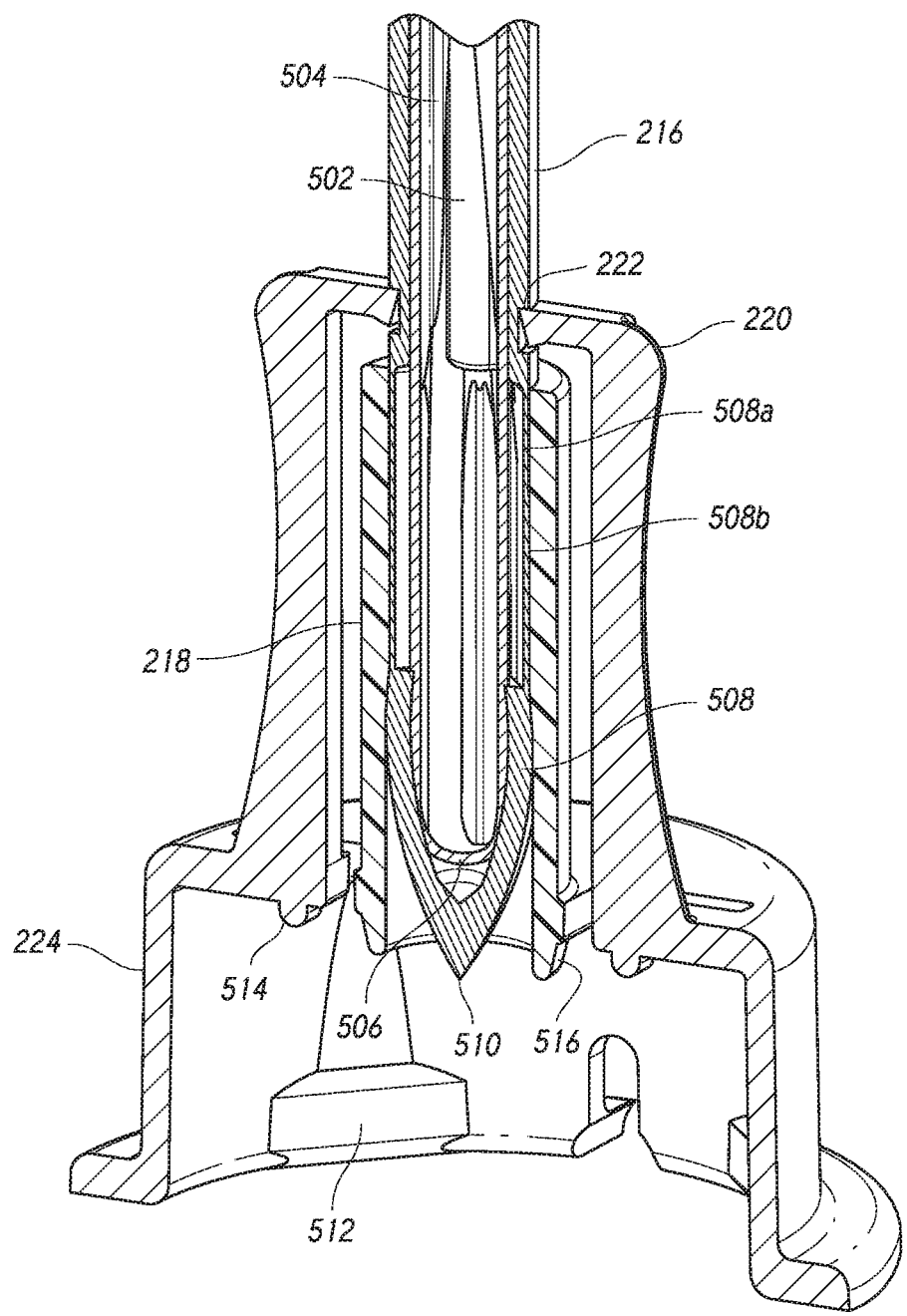
FIG. 5 is a partial cutaway view of the distal end of one embodiment of a vial adaptor in an initial stage.

FIG. 5 is a partial cutaway view of the distal end of an embodiment of a vial adaptor in an initial stage. Solely for the purposes of facilitating easier comprehension, it may be helpful to view FIG. 4 in light of the illustrated embodiment of FIG. 4.

In certain embodiments, the insertion member 216 may define or at least partially enclose one or more channels. In the illustrated embodiment, the insertion member 216 defines an extractor channel 502 and a regulator channel 504. The insertion member 216 may have an inner wall which separates and defines an inner boundary between the extractor channel 502 and a regulator channel 504.

In some configurations, the regulator channel 504 may extend through the insertion member 216 and may be connected to one or more regulator apertures. In some configurations, the regulator channel 504 extends through the insertion member 216 from the regulator aperture 204 to the distal end of the insertion member 216. The role of the regulator apertures in stabilizing pressure within the vial is described in more detail in regards to FIG. 10.

In some configurations, the extractor channel 502 may extend through the insertion member 216 and may comprise one or more extractor apertures. In some configurations, the extractor channel 502 extends through the insertion member 216 from an extractor aperture in medical connector interface 240 to an extractor aperture at the distal end of the insertion member 216, which is only exposed to the contents of the vial when the adaptor 200 is transitioned to its subsequent stage. The roles of the extractor apertures are provided in more detail in regards to FIG. 11.

In certain embodiments, the adaptor 200 comprises a piercing member 508. As previously mentioned, in some embodiments, the piercing member 508 and the insertion member 216 may be a single unit and integrally formed of a unitary piece of material. In other configurations, the insertion member 216 and the piercing member 508 may be distinct units that are mechanically coupled in substantially airtight engagement. For example, the distal end of the insertion member 216 may be attached to the proximal base of the piercing member 508.

In some embodiments, the piercing member 508 comprises a proximal portion 508*a* and a distal portion 508*b*. In some embodiments, the proximal portion 508*a* of the piercing member 508 is attached to the insertion member 216. In some embodiments, the distal portion 508*b* of the piercing member 508 is configured to pierce the septum of the vial as the insertion member 216 is forced downwards through the insertion member channel 218. As the distal portion 508*b* pierces the vial, the proximal portion 508*a* slides downwards through the insertion member channel 218 and may follow the distal portion 508*b* into the vial. Once the distal portion 508*b* of the piercing member is fully within the vial, the distal portion 508*b* of the piercing member 508 may be configured to separate within the vial. More specifically, the distal portion 508*b* of the piercing member may separate into two or more segments while the proximal portion 508*a* of the piercing member 508 does not separate. This feature of the piercing member 508 is illustrated and described in regards to FIG. 9.

In some embodiments, the adaptor 200 is configured to work with small vials. In some of such embodiments, the adaptor 200 is configured to work with small vials containing less than about 20 milliliters of liquid. In other embodiments, the adaptor 200 is configured to work with small vials containing less than about 10 milliliters of liquid. In yet other embodiments, the adaptor 200 is configured to work with small vials containing between about 10 milliliters to 20 milliliters of liquid. In order for the adaptor 200 to work with small vials, some of the dimensions of the adaptor 200 that must be specifically configured include the diameter of the insertion member 216, the diameter of the piercing member 508, the length of the piercing member 508, and the length that the insertion member 216 must be moved to transition the adaptor 200 from the initial stage to its subsequent stage. These dimensions must be carefully chosen so that the piercing member 508 and/or the insertion member 216 can both pass easily through the septum (which may be small) and fit comfortably within the body of the small vial.

The piercing member 508 and/or the insertion member 216 may be generally sized and dimensioned to fit within a vial, and in some instances they may be sized to fit within the narrow diameter of a small vial. Accordingly, in various embodiments, the diameter of the piercing member 508 or the insertion member 216 may be less than or equal to 0.25 inches. In other embodiments, the diameter may be less than or equal to 0.1875 inches. In still other embodiments, the diameter may be less than or equal to 0.125 inches. In some embodiments, the diameter may be less than or equal to 0.0625 inches.

The piercing member 508 and/or the insertion member 216 may be generally sized and dimensioned to be inserted through the septum of a vial without breaking and, in some instances, with relative ease. Accordingly, in various embodiments, the piercing member 508 or the insertion member 216 have a cross-sectional area of between about 0.025 and about 0.075 square inches, between about 0.040 and about 0.060 square inches, or between about 0.045 and about 0.055 square inches. In other embodiments, the cross-sectional area is less than about 0.075 square inches, less than about 0.060 square inches, or less than about 0.055 square inches. In still other embodiments, the cross-sectional area is greater than about 0.025 square inches, greater than about 0.035 square inches, or greater than about 0.045 square inches. In some embodiments, the cross-sectional area is about 0.050 square inches.

The piercing member 508 and/or the insertional member 216 may be generally sized and dimensioned to be inserted through the septum of a small vial with relative ease. Accordingly, in various embodiments, the piercing member 508 or the insertion member 216 have a cross-sectional area between about 0.040 and 0.060 square inches, between about 0.015 and 0.035 square inches, between about 0.005 and 0.020 square inches, or between about 0.001 and 0.005 square inches. In other embodiments, the cross-sectional area is less than about 0.060 square inches, less than about 0.035 square inches, less than about 0.020 square inches, or less than about 0.005 square inches. In other embodiments, the cross-sectional area is more than about 0.040 square inches, more than about 0.015 square inches, more than about 0.005 square inches, or more than about 0.001 square inches.

The piercing member 508 can be substantially cylindrical, as shown, or it can assume other geometric configurations. In some instances, the piercing member 508 tapers towards a distal end. In some arrangements, the distal end of the piercing member 508 defines a point that can be centered with respect to an axis of the piercing member 508 or offset therefrom. In certain embodiments, the distal end is angled from one side of the piercing member 508 to the opposite side. The piercing member 508 can comprise a rigid material, such as metal or plastic, suitable for insertion through a septum or cap of a vial. In certain embodiments, the piercing member 508 comprises polycarbonate plastic.

In some configurations, the piercing member 508 comprises a tip 510. In some configurations, the piercing portion 508b of the piercing member 508 comprises the tip 510. The tip 510 can have a variety of shapes and configurations. In some instances, the tip 510 is configured to facilitate insertion of the piercing member 508 through the septum or the cap of a vial. As illustrated, the tip 510, or a portion thereof, can be substantially conical, coming to a point at or near the axial center of the piercing member 508. In some configurations, the tip 510 may be located at the distal end of piercing member 508. In some configurations, the tip 510 angles from one side of the piercing member 508 to the other. In some configurations, the tip 510 and the piercing member 508 are permanently joined, and can be integrally formed. In various embodiments, the tip 510 comprises acrylic plastic, ABS plastic, or polycarbonate plastic.

The piercing member 508 may assume any of a number of cross-sectional geometries, such as, for example, oval, ellipsoidal, square, rectangular, hexagonal, or diamond-shaped. The cross-sectional geometry of the piercing member 508 can vary along a length thereof in size and/or shape. In some embodiments, the piercing member 508 has substantially circular cross-sections along a substantial portion of a length thereof. A circular geometry provides the piercing member 508 with substantially equal strength in all radial directions, thereby preventing bending or breaking that might otherwise occur upon insertion of the piercing member 508. The symmetry of an opening created in the septum by the circular piercing member 508 prevents pinching that might occur with angled geometries, allowing the piercing member 508 to more easily be inserted through the septum. Advantageously, the matching circular symmetries of the piercing member 508 and the opening in the septum ensure a tight fit between the piercing member 508 and the septum, even if the adaptor is inadvertently twisted. Accordingly, the risk of dangerous liquids or gases escaping the vial, or of impure air entering the vial and contaminating the contents thereof, can be reduced in some instances with a circularly symmetric configuration.

In some embodiments, the piercing member 508 is hollow. Portions of the piercing member 508 may have inner and outer surfaces that substantially conform to each other to provide that portion of the piercing member 508 with substantially uniform thickness. Additionally, in some embodiments, portions of the piercing member 508 may have varying thickness as the inner surface of the piercing member 508 varies in configuration from that of the outer surface of the piercing member 508. In the illustrated embodiment, the lower half of the piercing member 508 can be seen as having a substantially uniform thickness, while the upper half of the piercing member 508 can be seen as having a smaller substantially uniform thickness. In various embodiments, the thickness of a given portion of the piercing member 508 may be between about 0.001 inches and 0.080 inches, between about 0.020 inches and 0.060 inches, or between about 0.030 inches and about 0.050 inches. In other embodiments, the thickness of a portion of the piercing member 608 is greater than about 0.001 inches, greater than about 0.020 inches, or greater than about 0.030 inches. In still other embodiments, the thickness is less than about 0.080 inches, less than about 0.060 inches, or less than about 0.050 inches. In some arrangements, the cross-section of the inner surface of the piercing member 508 is shaped differently from that of the outer surface. The shape and thickness of various portions of the piercing member 508 can be altered to optimize the strength of the individual portions of the piercing member 508.

Similarly, the insertion member 216 may also have portions with substantially uniform thickness. In some embodiments, the thickness of a given portion of the insertion member 216 may be between about 0.001 inches and 0.080 inches, between about 0.020 inches and 0.060 inches, or between about 0.030 inches and about 0.050 inches. In other embodiments, the thickness of a portion of the insertion member 216 is greater than about 0.001 inches, greater than about 0.020 inches, or greater than about 0.030 inches. In still other embodiments, the thickness is less than about 0.080 inches, less than about 0.060 inches, or less than about 0.050 inches.

The length of the piercing member 508 may be configured to fully pierce the septum of the vial with ease and fit comfortably within a small vial. Certain small vials may have smaller height and may require a shorter piercing member 508. If the piercing member 508 is too long, it may break through the bottom of the vial or, if the piercing member 508 is configured to deploy into an open configuration (described further in regards to FIG. 8), the piercing member 508 may not fully deploy. However, at the same time there may be vials with thicker septa. For example, vials with thick septa are commonly found in Japan. If the piercing member 508 is too short, it will fail to fully pierce through the septum and will not deploy within the vial. Thus, the length of the piercing member 508 must be carefully configured to allow the adaptor 200 to be used with small vials.

In some instances, the length of the piercing member 508 may be between about 0.3 inches to about 1.3 inches, between about 0.5 inches and about 1.1 inches, or between about 0.7 inches and 0.9 inches. In other instances the length is greater than about 0.3 inches, greater than about 0.5 inches, or greater than about 0.7 inches. In still other instances, the length is less than about 1.3 inches, less than about 1.1 inches, or less than about 0.9 inches.

The length that the insertion member 216 must be moved to transition the adaptor 200 from the initial stage to its subsequent stage may also be configured so that the piercing member 508 can fully pierce the septum of the vial and fit comfortably within a small vial. If the travel distance is too long, the piercing member 508 may break through the bottom of the vial. If the travel distance is too short, the piercing member 508 may not fully pierce the septum or may fail to deploy within the vial. Looking at FIG. 1, it can be seen that the length the insertion member 216 must be moved for the adaptor 200 to transition into a subsequent stage is a function of the distance between the notches 222 and the tabs 214 that securely engage the engagement members 220. This distance is also directly related to the length of the insertion member 216.

The distance of travel between the notches 222 and the tabs 214 must be at least greater than the thickness of the septum added to the length of the distal portion 508b of the piercing member 508 if the piercing member 508 is to fully open or deploy within the vial. Otherwise, some of the distal portion 508b of the piercing member 508 would remain lodged in the septum and the piercing member 508 would be held closed. In some embodiments, the distance of travel between the notches 222 and the tabs 214 is between about 0.4 inches to 2 inches, between about 0.6 inches to 1.6 inches, or between about 0.8 inches to 1.2 inches. In other instances the length is greater than about 0.4 inches, greater than about 0.6 inches, or greater than about 0.8 inches. In still other instances, the length is less than about 2.0 inches, less than about 1.6 inches, or less than about 1.2 inches.

In certain embodiments, the adaptor may comprise a reservoir 506. In some configurations, the reservoir 506 may be shaped and sized to fit within the insertion member 216 and/or the piercing member 508 without folding. In some of such configurations, the distal portion of the reservoir 506 may be shaped and sized to fit—without folding—within the piercing member 508 when the distal portion 508b of the piercing member 508 is held in a closed configuration. In some configurations, undulations in the reservoir 506 may allow the reservoir 506 to fit more compactly into the piercing member 508. The reservoir 506 may be undulated in a star-like manner having multiple arms. Each arm may be folded, rolled, crumpled, or otherwise manipulated to fit within the piercing member 508 when closed. In other configurations, the reservoir 506 may be molded or shaped such that it naturally has a star-shaped cross-section and is capable of expanding to fill substantially cylindrical vials. The reservoir 506 is generally configured to expand, compress, and/or contract, and can comprise any of a wide variety of materials, including Mylar®, polyester, polyethylene, polypropylene, saran, latex rubber, polyisoprene, silicone rubber, and polyurethane. In some embodiments, the reservoir 506 comprises a material capable of forming a substantially airtight seal with the insertion member 216. In other embodiments, the reservoir 506 comprises a material that can be adhered to the insertion member 216 in substantially airtight engagement. In yet other embodiments, the reservoir 506 comprises a material capable of forming a substantially airtight seal with the piercing member 508 or can be adhered to the piercing member 508 in substantially airtight engagement. In many instances, the reservoir 506 comprises a material that is generally impervious to liquid and air. In certain embodiments, it is preferred that the reservoir 506 comprise a material that is inert with respect to the intended contents of the vial. In some embodiments, the reservoir 506 comprises latex-free silicone having a durometer between about 10 and about 40. In some embodiments, the reservoir 506 resembles the structure shown in FIG. 16 of, and described in, the specification of U.S. Pat. No. 7,883,499, titled "VIAL ADAPTORS AND VIALS FOR REGULATION PRESSURE", filed Mar. 7, 2008, the entire contents of which are hereby incorporated by reference herein and are made a part of this specification.

The reservoir 506 may be attached to the insertion member 216 by any suitable means. In some configurations, the reservoir 506 may be secured to an end of the insertion member 216 or to the interior of the insertion member 216 by any suitable method. In some configurations, only the proximal end of the reservoir 506 is secured to the insertion member 216, freeing the remainder of the reservoir 506 to expand. Suitable means for securing the reservoir 506 to the insertion member 216 may include the methods described with respect to attaching the insertion member 216 to the piercing member 508, with some examples including by adhesive, a heat seal, a tension fit, and so forth.

In some configurations, at least the proximal end (not shown) of the reservoir 506 is in substantially airtight engagement with the insertion member 216. In some instances, a substantially airtight seal is achieved when the proximal end of the reservoir 506 is thicker than other portions of the reservoir 506 and fits more snugly within the insertion member 216 than the remainder of the reservoir 506. In certain instances, the thicker proximal end of the reservoir 506 comprises a higher durometer material than the remainder of the reservoir 506. In some instances, the proximal end comprises latex-free silicone having a durometer between about 40 and about 70. In other instances, the proximal end of the reservoir 506 is retained in the insertion member 216 by a plastic sleeve (not shown) that presses the proximal end against the insertion member 216. In still further instances, the proximal end of the reservoir 506 is adhered to the insertion member 216 by any suitable manner, such as by heat sealing or gluing. In some embodiments, a greater portion of the reservoir 506 than just the proximal end is in substantially airtight contact with the insertion member 216. In some embodiments, a reservoir flange (not numbered) is located at the proximal end of the reservoir 506. A method of manufacturing the adaptor 200 may include inserting the reservoir 506 into the insertion member 216 such that the reservoir flange (not numbered) rests on the proximal end of the insertion member 216. The handle 208 may then be attached to the proximal end of the insertion member 216 such that the reservoir 506 is secured through a friction-fit engagement of the reservoir flange (not numbered) between the proximal end of the insertion member 216 and the handle 208.

In various configurations, the reservoir 506 may have varying sizes and thicknesses, and it may be configured to be expandable to varying sizes and thicknesses. In some configurations, the reservoir 506 is sized to fit within both the insertion member 216 and the piercing member 508 without folding. Accordingly, the reservoir 506 may have a smaller diameter than both the insertion member 216 and the piercing member 508 in order to fit within them. In some configurations, the reservoir 506 may have a substantially smaller diameter than the insertion member 216 and/or the piercing member 508. Thus, in some configurations, the reservoir 506 may have a diameter less than or equal to 0.25 inches, 0.1875 inches, 0.125 inches, or 0.0625 inches.

In some embodiments, the reservoir 506 is sized and configured to expand to substantially fill the vial. For example, in some arrangements, the reservoir 506 comprises a flexible, expandable material sized and configured to expand to fill a substantial portion of the volume within the vial. In some instances, the reservoir 506 is expandable to substantially fill a range of volumes such that a single adaptor can be configured to operate with vials of various sizes. In some embodiments, the reservoir 506 is configured to fill at least about 25, 30, 35, 40, 45, 50, 60, 70, 80, or 90 percent of one vial. In other embodiments, the reservoir 506 is configured to fill a volume equal to at least about 30, 40, 45, 50, 55, 60, 65, 70, 75, 80, 85, or 90 percent of the volume of fluid contained within the vial prior to the coupling of the adaptor and the vial. In some embodiments, the reservoir 506 is configured to fill a volume equal to about 70 percent of the volume of fluid contained within the vial prior to the coupling of the adaptor 200 and the vial 210. In other embodiments, the reservoir 506 is configured to fill at least about 25, 30, 35, 40, 45, 50, 60, 70, 80, or 90 percent of a first vial having a first volume, and at least about 25, 30, 35, 40, 45, 50, 60, 70, 80, or 90 percent of a second vial having a second volume larger than the first volume. In some embodiments, the reservoir is sized, shaped, and/or is sufficiently flexible to fill a substantial volume of a vial that has a capacity of at most about 10 milliliters or at most about 20 milliliters, In certain arrangements, there may be fluid communication between the interior of the reservoir 506 and the environment surrounding the adaptor. In some configurations, the interior of the reservoir 506 may be in fluid communication with the environment surrounding the adaptor through a regulator aperture. The regulator aperture is shown and discussed in further detail in regards to FIG. 11.

In certain arrangements, the reservoir 506 may be specifically shaped so that the entire reservoir 506 is located within the insertion member 216 and/or the piercing member 508 when the adaptor is in its initial stage. In some arrangements, the reservoir 506 may even remain within the insertion member 216 and the piercing member 508 when the adaptor is being coupled to the vial. Accordingly, the reservoir 506 is generally protected by the piercing member 508 from rips or tears when the piercing member 508 is inserted in the vial. In some arrangements, the reservoir 506 may reside within the regulator channel 504 defined by the insertion member 216 and/or the piercing member 508. In some of such arrangements, the reservoir 506 resides in the regulator channel 504 but not the extractor channel 502. Accordingly, in some embodiments, the proximal end of reservoir 506 may have a horse shoe shaped cross section that allows it to fit around the extractor channel 502 and within the regulator channel 504. Thus, in some embodiments the reservoir 506 fits within the regulator channel 504 in the insertion member 216 and the piercing member 508 when the adaptor is in its initial stage. In some embodiments, the reservoir 506 is symmetric about a longitudinal plane passing through a center of the reservoir 506.

It may be desirable for the reservoir 506 to be configured with a length that allows reservoir 506 to span the entire length of the insertion member 216 and have a distal portion that fits inside the piercing member 508 without folding. Thus, it may be desirable to for the maximum length of the reservoir 506 to be the length of the insertion member 216 added to the length of the piercing member 508. In some embodiments, the height of the reservoir 506 may be from about 0.75 to 5.25 inches, from about 1.25 to 3.75 inches, or from about 1.75 to 2.75 inches. In other configurations, the height is at least about 0.75 inches, at least about 1.25 inches, or at least about 1.75 inches. In still other configurations, the height is no more than about 5.25 inches, no more than about 3.75 inches, or no more than about 2.75 inches. In some embodiments, the height is about 2.00 inches.

In some embodiments, the distal portion of the reservoir 506 is generally cylindrical with a rounded distal end, as shown in FIG. 5. Cylindrical configurations can be advantageous for use with a vial that is largely cylindrical, as is often the case with standard medicinal vials, as it allows the reservoir 506 to expand to a shape that substantially conforms to the interior volume of the vial. However, the distal portion of the reservoir 506 may be any shape, such as for example, generally spherical, generally cylindrical, generally conical, substantially bulbous, generally rectangular, and generally triangular.

As previously mentioned, in some embodiments, the proximal portion of the reservoir 506 may have a concavely rounded cross-section or a horseshoe shape. This may allow the reservoir 506 to fit around the extractor channel 502. In the illustrated embodiment, the proximal portion of reservoir 506 has a concavely rounded cross section or a horseshoe shape and the distal portion of the reservoir 506 is generally cylindrical with a rounded distal end. The radius of curvature of the distal portion of the reservoir 506 may be larger than the radius of curvature of the concavely.

In some embodiments, at least the distal portion of the reservoir 506 comprises expandable material. In various arrangements, the distal portion in an unexpanded state has an outer diameter of between about 0.010 inches and about 0.600 inches, between about 0.030 inches and about 0.350 inches, or between about 0.050 inches and about 0.250 inches. In some arrangements, the outer diameter is greater than about 0.010, greater than about 0.030 inches, or greater than about 0.050 inches. In other arrangements, the outer diameter is less than about 0.600 inches, less than about 0.350 inches, or less than about 0.250 inches. In various arrangements, the distal portion 268 in an unexpanded state has a height of between about 0.30 inches to about 1.30 inches, between about 0.50 inches and about 1.10 inches, or between about 0.70 inches and 0.90 inches. In some arrangements, the height is greater than about 0.30 inches, greater than about 0.50 inches, or greater than about 0.70 inches. In other arrangements, the height is less than about 1.30 inches, less than about 0.1.10 inches, or less than about 0.90 inches. In some arrangements, the height is about 0.75 inches.

In some embodiments, the reservoir 506, or the distal portion of the reservoir 506, has walls with a thickness between about 0.001 inches and 0.004 inches, between about 0.0005 inches to about 0.010 inches, between about 0.001 inches and about 0.002 inches, between about 0.002 inches and about 0.003 inches, or between about 0.003 inches and about 0.004 inches thick. In some embodiments, the walls have a thickness between about 0.001 and 0.025 inches, between about 0.001 and 0.010 inches, or between about 0.010 and 0.025 inches. In other arrangements, the walls are greater than 0.0005 inches, greater than 0.001 inches, greater than 0.002 inches, greater than 0.003 inches, greater than 0.005 inches, greater than about 0.010 inches, greater than about 0.015 inches, or greater than about 0.020 inches thick. In still other arrangements, the walls are less than about 0.025 inches, less than about 0.020 inches, less than about 0.015 inches, less than about 0.010 inches, less than about 0.005 inches, less than about 0.004 inches, less than about 0.003 inches, or less than about 0.002 inches thick. In some embodiments, the thickness of the walls is about 0.015 inches.

In many arrangements, the reservoir 506 is sufficiently thick to resist tearing or puncturing during manufacture or use, but sufficiently flexible to contract under relatively small pressure differentials, such as pressure differentials no more than about 1 psi, no more than about 2 psi, no more than about 3 psi, no more than about 4 psi, or no more than about 5 psi.

In certain embodiments, the cap connector 224 comprises one or more projections 512 that aid in securing the adaptor 200 to the vial. The one or more projections 512 extend toward an axial center of the cap connector 224. In some configurations, the one or more projections 512 comprise a single circular flange extending around the interior of the cap connector. The cap connector 224 can be sized and configured such that an upper surface of the one or more projections 512 abuts a lower surface of the cap, ridge, or neck of a vial, helping secure the adaptor 200 in place. In some embodiments, the projections 512 may fit into a groove formed by two different features on the vial, such as a space between the lower surface of the cap and a ridge on the neck of the vial, helping secure the adaptor 200 in place.

The one or more projections 512 can be rounded, chamfered, or otherwise shaped to facilitate the coupling of the adaptor and the vial. For example, as the adaptor having chamfered projections 512 is introduced to the vial, a lower surface of the chamfered projections 512 abuts a top surface of the cap of the vial. As the adaptor is advanced onto the vial, the rounded surfaces cause the cap connector 224 to expand radially outward. As the adaptor is advanced further onto the vial, a resilient force of the deformed cap connector 224 seats the projections 512 under the cap, ridge, or neck of the vial, thus securing the adaptor in place.

In certain embodiments, the cap connector 224 may comprise a lip 516. In other embodiments, the insertion member channel 218 may comprise the lip 516. The lip 516 is configured to keep the tip 510 of the piercing member 508 barely touching the septum of the vial when the adaptor 200 is coupled to the vial. This feature can be seen in FIG. 6, which shows the septum of the vial pressed against the lip 516 and the tip of piercing member 508 barely touching the septum of the vial.

In certain embodiments, the cap connector 224 may comprise one or more projections 514. The projections 514 may be one or more projections, bumps, and so forth, that may be located under the base of the engagement members 220. When the vial is fully coupled to the adaptor 200, the cap of the vial may push against the projections 514 and trigger the engagement member unlock 230 mechanism. Pushing against the projections 514 may push outward the portions of the cap connector 224 connected to the bases of the engagement members 220. As shown in the illustration, this causes the engagement members 220 to re-position and no longer be engaged with notches 222. Thus, the projections 514 may be configured to disengage the engagement members 220 only upon fully coupling the adaptor 200 to the vial, allowing the adaptor 200 to transition from its initial stage to its subsequent stage.

In some embodiments, there may be a seal (not shown) that resides between the insertion member channel 218 and the insertion member 216. The seal may be located at any point along the internal surface of the insertion member channel 218. The seal may be designed to keep vapors and liquids from leaking out between the insertion member channel 218 and the insertion member 216 during insertion of the insertion member 216 into the vial, or when contents are being added or withdrawn to the vial. In some embodiments, once the insertion member 216 is inserted into the vial, the seal may lock into place and be immovable. The seal may comprise any suitable material for forming a substantially airtight seal with the insertion member channel 218 and the insertion member 216. In some configurations, the seal comprises polyethylene. In some embodiments, the seal comprises an o-ring.

Figure 6:
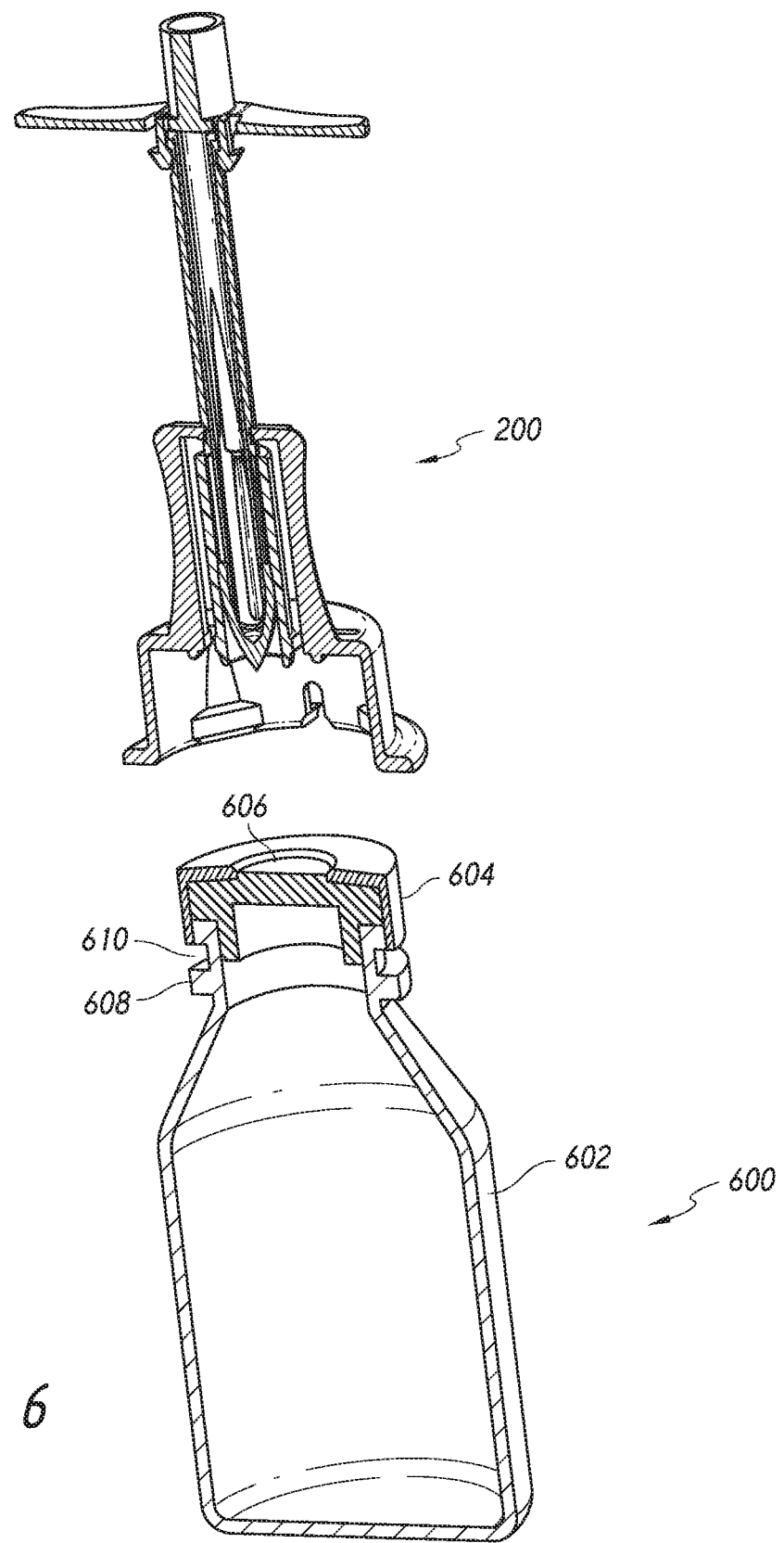
FIG. 6 is a cutaway view of one embodiment of a vial adaptor in an initial stage and a vial.

FIG. 6 is a cutaway view of a vial adaptor 200 in an initial stage and a vial 600.

The vial 600 may contain a medical fluid and/or a relatively small amount of sterilized air. The vial 600 can comprise any suitable container for storing medical fluids. In some instances, the vial 600 comprises any of a number of standard medical vials known in the art, such as those produced by Abbott Laboratories of Abbott Park, Ill. Preferably, the vial 600 is capable of being hermetically sealed. In some embodiments, vial 600 may contain a powder, a concentrated liquid, or some other substance that is diluted prior to administration thereof to a patient. Accordingly, in certain embodiments, a diluent may need to be added to the vial 600 via the adaptor 200.

In some configurations, the vial 600 comprises a body 602, a cap 604, and a septum 606. The body 602 preferably comprises a rigid, substantially impervious material, such as plastic or glass. The septum 606 can comprise an elastomeric material capable of deforming in such a way when punctured by an item that it forms a substantially airtight seal around that item. For example, in some instances, the septum 606 comprises silicone rubber or butyl rubber. The thickness of the septum 606 may vary across embodiments. For example, in an American-style vial, the septum 606 may have a thin section in the center, whereas in a Japanese style vial, the septum 606 may have a greater thickness overall. In some embodiments, the cap 604 may be a thin metal casing that goes over the septum 606, or the septum 606 and part of the body 602.

In certain embodiments, the cap 604 may have a lower surface that extends outwardly from the top of the body 602. In some embodiments, the body 602 may have a ridge 608 that extends outwardly from the top of the body 602. In some of such embodiments, the ridge 608 and the lower surface of cap 604 may define a groove 610.

Figure 7:
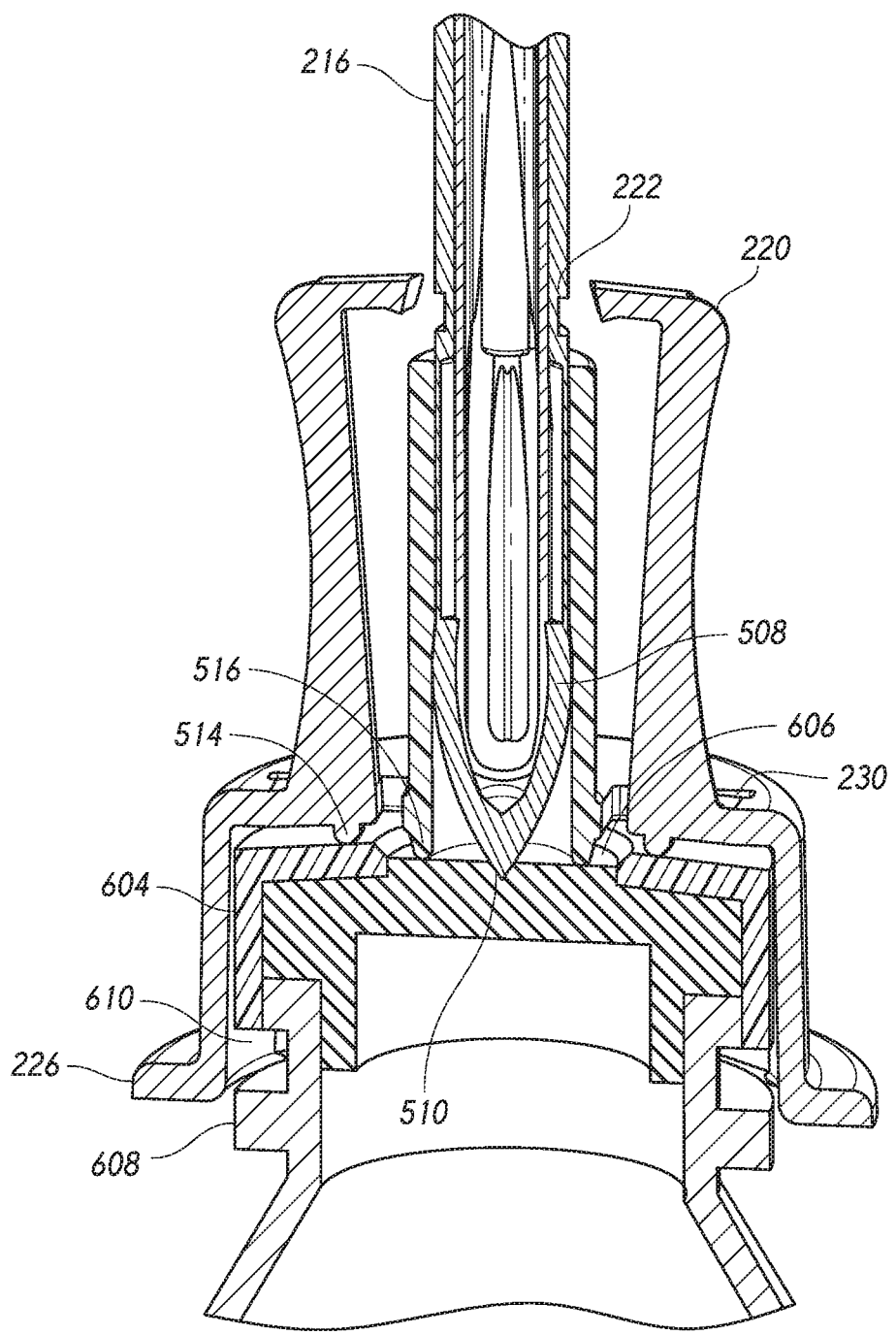
FIG. 7 is a partial cutaway view of one embodiment of a vial adaptor in an initial stage after it is coupled with a vial.

FIG. 7 is a partial cutaway view of a vial adaptor 200 in an initial stage after it is coupled with a vial 600.

In the illustrated embodiment, the cap connector 224 firmly secures the adaptor 200 to the cap 604. The lip 516 keeps the tip 510 of piercing member 508 barely touching the septum 606 of the vial 600 when the adaptor 200 is coupled to the vial 600. The piercing member 508 may abut, or be adjacent to, the septum 606 of the vial 600 when the adaptor 200 is coupled to the vial 600. The piercing member 508 is also shown to be oriented substantially perpendicularly with respect to the septum 606 when the adaptor 200 and the vial 600 are coupled. If the insertion path is also perpendicular to the septum 606 when the adaptor 200 and the vial 600 are coupled, then coupling the adaptor 200 to the vial 600 ensures that the piercing member 508 pierces straight into the septum 606 of the vial 600 due to both the orientation of the piercing member 508 and the insertion path being perpendicular. The cap 604 of the vial 600 pushes against the projections 514 in the cap connector 224, which causes the engagement members 220 to flex outwards and be disengaged from the notches 222 of the insertion member 216 due to the engagement member unlock 230 mechanism.

Now that the adaptor 200 is fully coupled to the vial 600 and the engagement members 220 are no longer engaged with the notches 222, the insertion member 216 is free to slide downwards to force the tip 510 of the piercing member 508 through the septum 606 of the vial 600. Thus, the insertion member 216 can only slide downwards to pierce the septum 606 when the adaptor 200 is fully coupled to the vial 600. This feature prevents angled insertions of the insertion member 216 into the vial 600.

Features of the adaptor 200, such as the previously described projections 512 inside the cap connector 224, may be securely engaged with the features of the vial 600. For example, the projections 512 inside the cap connector 224 may be configured such that an upper surface of the one or more projections 512 abuts the lower surface of the cap 604, securing the adaptor 200 from being pulled away from the vial 600.

In some configurations, the projections 512 may be configured to be seated in the groove 610 defined by the ridge 608 and the lower surface of the cap 604, securing the adaptor 200 from being pulled away from the vial 600 and being pushed further toward the vial 600. As shown in the illustrated embodiment, the engagement members 220 are flexed outwards enough to be disengaged from notches 222 and are able to securely engage the tabs 214 in their new outwardly flexed position. The engagement members 220 may be configured to be unable to disengage from the tabs 214 once securely engaged, which keeps the insertion member 216 fully inserted and the adaptor 200 in its subsequent stage. It may be desirable to prevent the adaptor 200 from being pushed further toward the vial 600 in this state, since doing so may further push the cap 604 against the projections 514. This could result in the engagement members 220 pushing further outwards to the point that they become disengaged from the tabs 214 and allowing the insertion member 216 to slide back out of the vial 600.

When a user is finished using the adaptor 200, the user may grasp the lip 226 in order to uncouple the adaptor 200 from the vial. In some configurations, grasping the lip 226 outwardly deforms the cap connector 224 and unseats the projections 512 of the cap connector 224 from the groove 610 or the lower surface of cap 604. This reduces the grip of the projections 512 on the vial 600 and allows the adaptor 200 to be pulled off.

Figure 8:
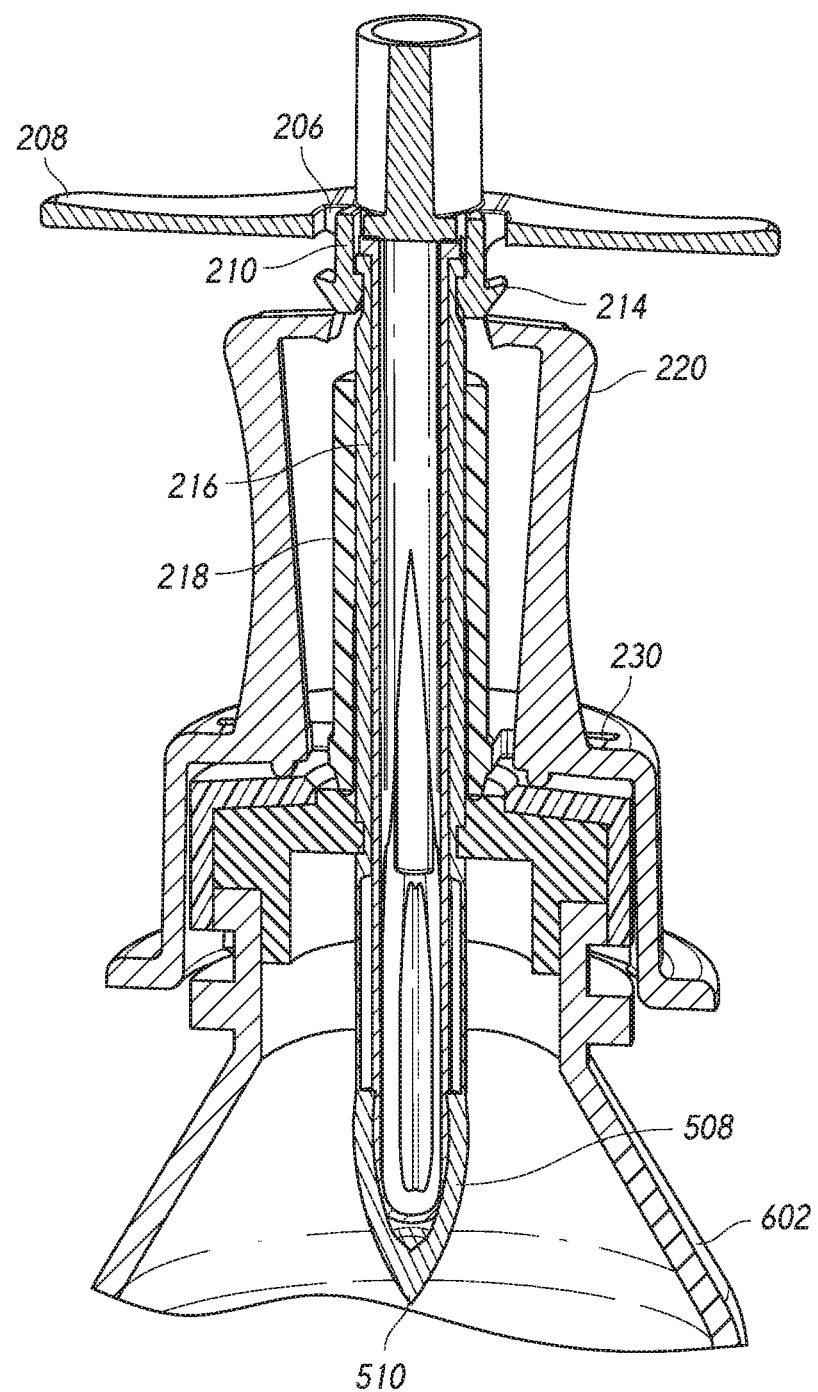
FIG. 8 is a partial cutaway view of one embodiment of a vial adaptor in transition from an initial stage to a subsequent stage after it is coupled with a vial.

FIG. 8 is a partial cutaway view of a vial adaptor 200 in transition from an initial stage to a subsequent stage after it is coupled with a vial 600.

As seen in the illustration, the insertion member 216 has been forced downwards through insertion member channel 218 to drive the tip 510 of piercing member 508 through the septum 606 of the vial 600 and inside the vial body 602. However, the insertion member 216 has not been fully inserted to the point that the piercing member 508 will deploy within the vial 600 and the adaptor 200 will be in its subsequent stage.

The engagement members 220 are seen flexed outwards and are no longer engaged with the insertion member 216 due to the engagement member unlock 230 mechanisms of adaptor 200. It should be noted that the engagement members 220 have been flexed outwards to the point where they no longer engage the notches 222 of insertion member 216 but are now in an ideal outward position that allows them to securely engage tabs 214 of locking ring 210 if insertion member 216 is pushed further into insertion member channel 218.

FIG. 8 also illustrates the openings 206 in the handle 208 at a different angle. From the viewing angle provided, it can be seen that a user looking downwards through the openings 206 can see the tabs 214 of the locking ring 210. In some embodiments, the engagement members 220 and the locking ring 210 are different colors so that a user may be able to determine if the engagement member 220 is securely engaged to the tabs 214 of locking ring 210 by quickly glancing through opening 206. For example, if the user sees the color of the engagement members 220 through the opening 206, the user can quickly know that the engagement members 220 are securely engaged to the tabs 214 and the insertion member 216 will not slip back out of the vial 600 to leak or spill the contents of the vial 600.

Figure 9:
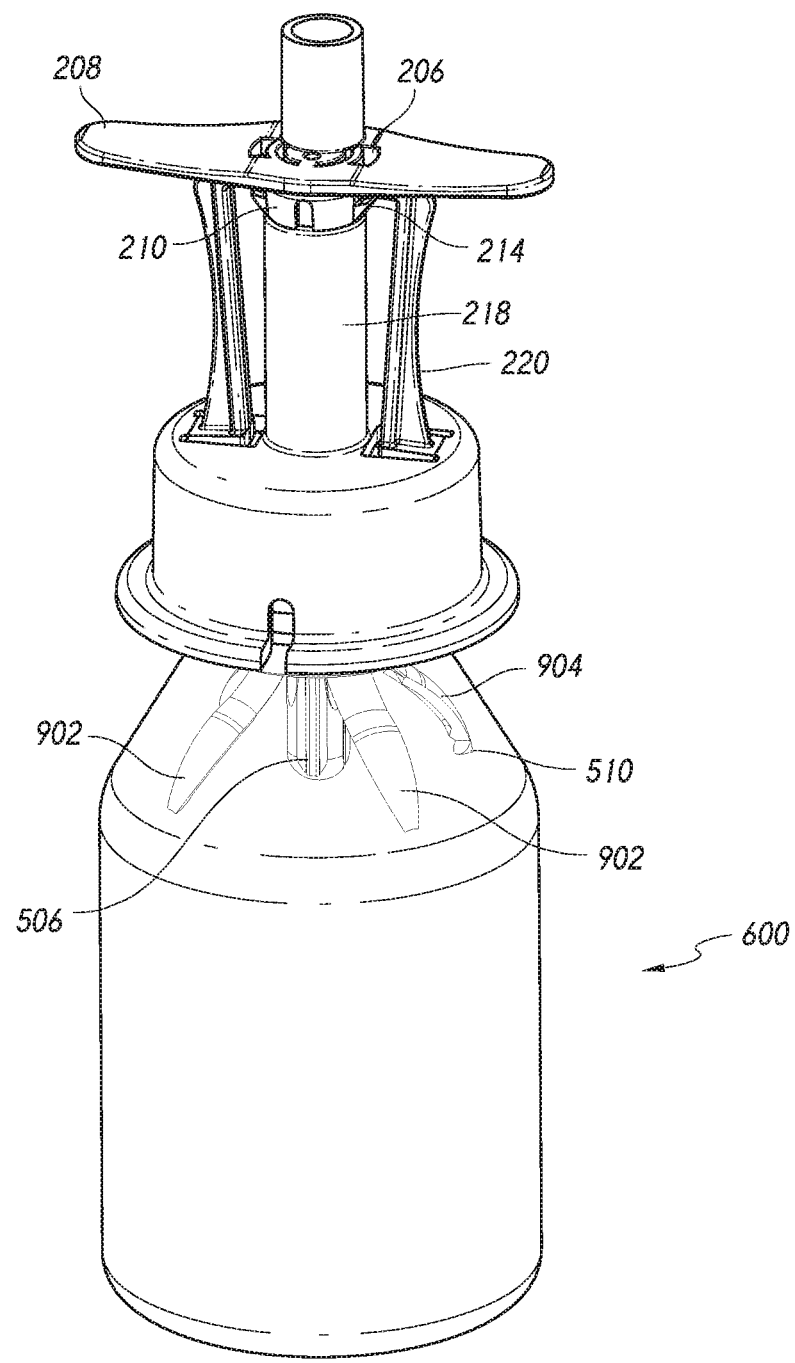
FIG. 9 is a perspective view of one embodiment of a vial adaptor in a subsequent stage after it is coupled with a vial.

FIG. 9 is a perspective view of a vial adaptor 200 in a subsequent stage after it is coupled with a vial 600.

FIG. 9 further demonstrates the usefulness of the openings 206 in the handle 208. In the illustration, the engagement members 220 are presumably securely engaged with the tabs 214 of the locking ring 210. However, from the viewing angle provided in the illustration, it is difficult to determine if the engagement members 220 are actually engaged with the tabs 214. Thus, the adaptor 200 may be configured to allow a user to quickly determine if the adaptor 200 is in its subsequent stage or if the engagement members 220 are securely engaged to the tabs 214.

In some embodiments, the piercing member 508 may comprise two or more separate members 902, 904. In the illustrated embodiment, the adaptor 200 is shown as having three separate members 902 and one separate member 904. In some configurations, the separate members 904 comprise the tip 510 of the piercing member 508. Thus, although there may be two or more total separate members 902, 904, there generally will be at least one separate member 904. In some configurations, the tip 510 is molded onto the one or more separate members 904. In some embodiments, the piercing member 508 may comprise a proximal portion 508*a* and a distal portion 508*b*, with the distal portion 508*b* comprising the two or more separate members 902, 904. In some embodiments, the separate members 902, 904 meet at the proximal portion 508*a* of the piercing member 508. In some configurations, the proximal portion 508*a* of piercing member 508 is fixed while the separate members 902, 904 are allowed to move.

In the initial stage of the adaptor 200, as shown in previous Figures, the separate members 902, 904 of the piercing member 508 are in a closed configuration. Combined, the separate members 902, 904 cooperatively house the distal portion of the reservoir 502 when the piercing member 508 is in the closed configuration. The distal portion of the reservoir 502 is sized and shaped to fit within the closed piercing member 508 without folding.

In certain embodiments, such as the one shown in FIG. 9, the separate members 902, 904 are biased toward an open configuration. In some instances, the bias is provided by the method used to create the separate members 902, 904. The separate members 902, 904 may be integrally formed from a unitary piece of molded plastic, and during the molding process they may be molded into their splayed, open configuration.

When the adaptor 200 is assembled, the separate members 902, 904 may be brought together into the closed configuration of the piercing member 508, which may be placed within the insertion member channel 218. The insertion member channel 218 holds the piercing member 508 in its closed configuration when part of the piercing member 508 is within the insertion member channel 218. When the piercing member 508 is in the closed configuration it has the tip 510, which comes from the one or more separate members 904. The other legs of the piercing member 508—the separate members 902—may fit flush with the tip 510 when the piercing member 508 is collapsed within the insertion member channel 218. Accordingly, the insertion member channel 218 may retain the separate members 902, 904—that are biased toward an open configuration—in a closed configuration so that the piercing member 508 may easily pierce the septum 606.

As the piercing member 508 enters the vial 600, it continues through the septum 606 until the piercing member 508 slides out of the insertion member channel 218 and returns to the biased configuration of which it was molded. In some embodiments, the piercing member 508 entering the vial 600 causes the separate members 902, 904 to return to their naturally open configuration. This may deploy the reservoir 506 within the vial 600, such that the reservoir 506 is exposed to the interior of the vial 600.

As previously mentioned, there may be any number of separate members 902 and at least one separate member 904. As shown in the illustration, the piercing member 508 is shown to be made up of a separate member 904 and three separate members 902, for a total of four separate members. In various configurations, the piercing member 508 may comprise two, three, four, five, six, seven, eight total separate members, and so forth.

In some embodiments, the separate members of the piercing member 508 may be referred to as "leaves" of the piercing member, with each separate member referred to as a "leaf". In general, the term "leaves" may be better understood as one or more components, extensions, members, and so forth that extend from a single "stem". Accordingly, in some embodiments the piercing member 508 may be seen as having multiple "leaves" (e.g., the separate members) that extend from the "stem" of the piercing member 508. In some of such embodiments, the leaves of the piercing member 508 may be biased towards a splayed configuration, such that the ends or tips of the leaves separate and diverge. Collapsing or moving the leaves together may bring the ends or tips of the leaves together.

In some configurations, the adaptor 200 is configured to work with small vials. Small vials may have a smaller height or narrower diameter. The lengths of the separate members 902, 904 as well as the angle at which the separate members 902, 904 deviate between their open and closed configuration may be configured such that the piercing member 508 in its fully open configuration may be able to fit within the vial.

In some configurations, the length of the separate members 902, 904 may be between about 0.250 inches to 1.0 inches, between about 0.40 inches to 0.80 inches, and between about 0.50 inches to 0.70 inches. In some configurations, the angle at which the separate members 902, 904 deviate between their open and closed configuration may be between about 10 degrees to 60 degrees, between about 20 degrees to 50 degrees, or between about 30 degrees to 40 degrees.

As noted above, in some instances the body 602 of the vial 600 comprises a substantially rigid material, such as glass or plastic. Accordingly, configurations wherein the reservoir 506 is deployed within the vial 600 advantageously shield the reservoir 506 from accidental snags, rips, or tears. Furthermore, configurations wherein the reservoir 506 is located within the vial 600 can have a lower center of mass than other configurations, which helps to prevent accidental tipping and spilling of the vial 600. Furthermore, since the insertion member 216 is locked into place once fully advanced into the vial, it generally cannot be withdrawn from the vial 600. This reduces the chance of puncturing or tearing the reservoir 506, such as the chance of collapsing the separate members 902, 904 around the reservoir 506 after the reservoir 506 has been deployed.

Figure 10:
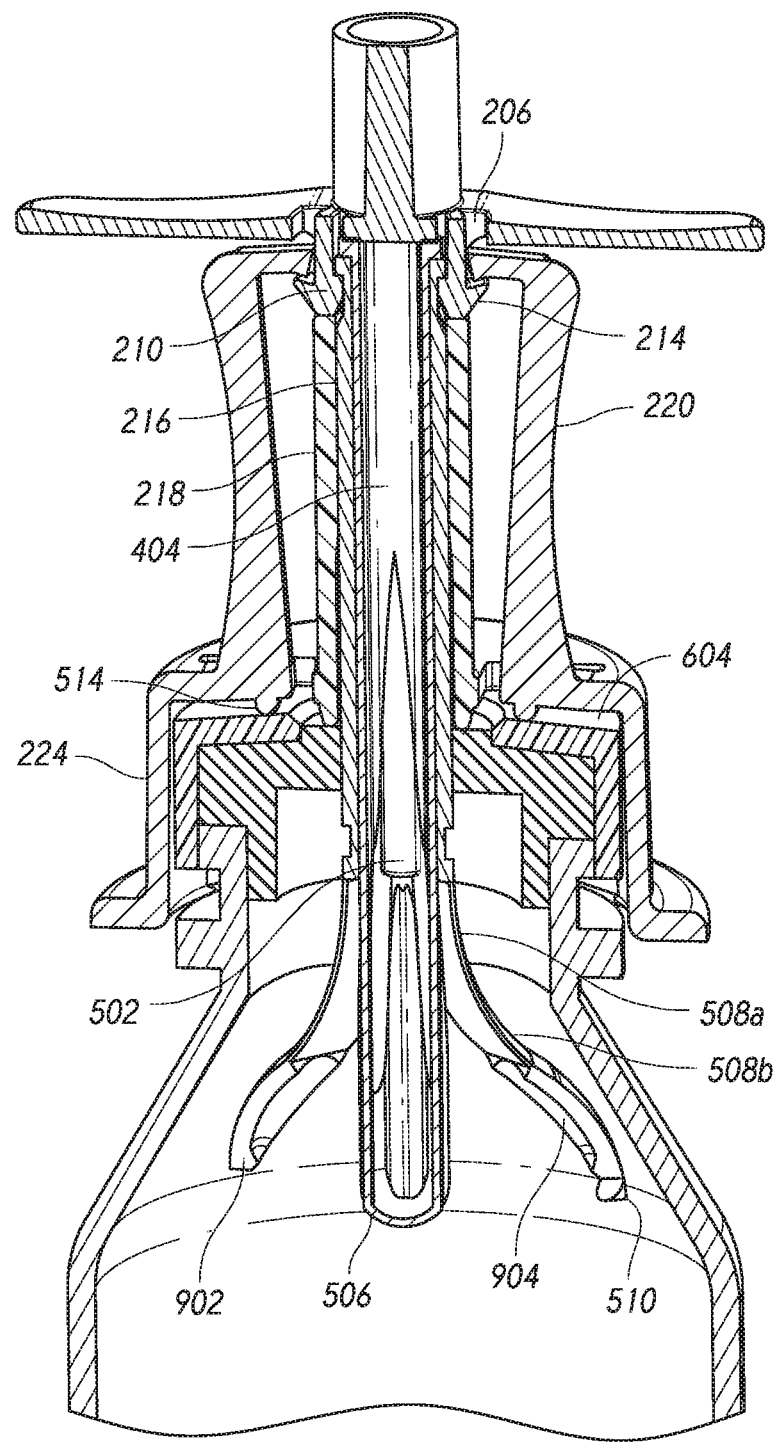
FIG. 10 is a partial cutaway view of one embodiment of a vial adaptor in a subsequent stage after it is coupled with a vial.

FIG. 10 is a partial cutaway view of a vial adaptor 200 in a subsequent stage after it is coupled with a vial 600.

In this subsequent stage, the cap 604 can be seen pressing against the projections 514 which push the engagement members 220 outward. With the engagement members 220 in this outwardly flexed position, they are now able to be securely engaged with the tabs 214. The engagement members 220 will remain securely engaged with the tabs 214 to lock the adaptor 200 in this subsequent stage, even if the cap connector 224 is pulled off of the vial 600. The engagement members 220 also prevent the insertion member 216 from sliding back out of the vial 600 through the insertion member channel 218.

The distal portion 508b of the piercing member 508 is in an open configuration. The distal portion 508b has separated into the separate members 902, 904. In the illustration, only one separate member 902 is shown. The tip 510 is located at the distal end of the separate member 904.

In this subsequent stage, the reservoir 506 has been deployed and is now exposed to the interior of the vial 600. The regulator channel 504 may be in fluid communication with the surrounding ambient air and the reservoir 506. However, the reservoir 506 may comprise a substantially impervious material, such that the fluid and the air inside the vial 600 do not contact air outside the vial—for example, ambient air inside the reservoir 506.

In the illustrated embodiment, the extractor channel 502 extends through the insertion member 216 such that the extractor aperture of the extractor channel 502 is located within, or at a position interior to an outer surface of, the insertion member 216. However, in some configurations the extractor aperture is located within, or at a position interior to an outer surface of, the piercing member 508. In certain embodiments, as shown, when the adaptor 200 is in its subsequent stage and the piercing member 508 is in the open configuration, the extractor aperture at the distal end of extractor channel 502 becomes exposed to the interior of the vial 600. This allows the contents of the vial 600 to be withdrawn through the extractor channel 502.

In some configurations, the extractor aperture at the distal end of the extractor channel 502 may be oriented to not be along a surface of the extractor channel 502 that engages either the reservoir 506 or the septum 606 of the vial 600. In some configurations, the extractor aperture at the distal end of extractor channel 502 may be an opening at the axial end of extractor channel 502 or a horizontal opening with respect to the septum 606 of the vial 600. Advantageously, that positioning of the extractor aperture prevents the extractor aperture from being blocked by the septum 606 of the vial 600 and makes it less likely that the extractor aperture would be blocked by an expanding reservoir 506.

In some instances, it is desirable to remove substantially all of the fluid within the vial 600, such as when the fluid is a costly medication. Accordingly, in certain arrangements, the distal extractor aperture of the extractor channel 502 may be as close as possible to the septum 606 of the vial 600, such as adjacent or flush with the interior surface of the septum, when the adaptor 200 is in its subsequent stage, or when the insertion member 216 is fully inserted into the vial 600. Advantageously, this permits the distal extractor aperture to withdraw most or all of the liquid from the vial 600 through the extractor channel 502.

Once the adaptor 200 is in the subsequent stage, the locking ring 210 may be at the proximal end of the insertion member channel 218. In some configurations, the locking ring 210 may form a substantially airtight engagement with the insertion member channel 218 due to the tension on the locking ring 210 from the engagement arms 220. The locking ring 210 becomes locked into place and is not removable because the tabs 214 of the locking ring 210 securely engage the engagement members 220. The secure engagement between the tabs 214 and the engagement members 220 also locks the insertion member 216 into place and prevents it from sliding through the insertion member channel 218 or being withdrawn from the vial 600.

In some configurations, the locking ring 210 may comprise a seal or any suitable material for forming a substantially airtight seal with the insertion member channel 218. In some instances, the locking ring 210 may comprise a standard O-ring as known in the art. Thus, in some configurations, the locking ring 210 may keep vapors and liquids in the vial from leaking out from between the insertion member 216 and the insertion member channel 218.

Figure 11:
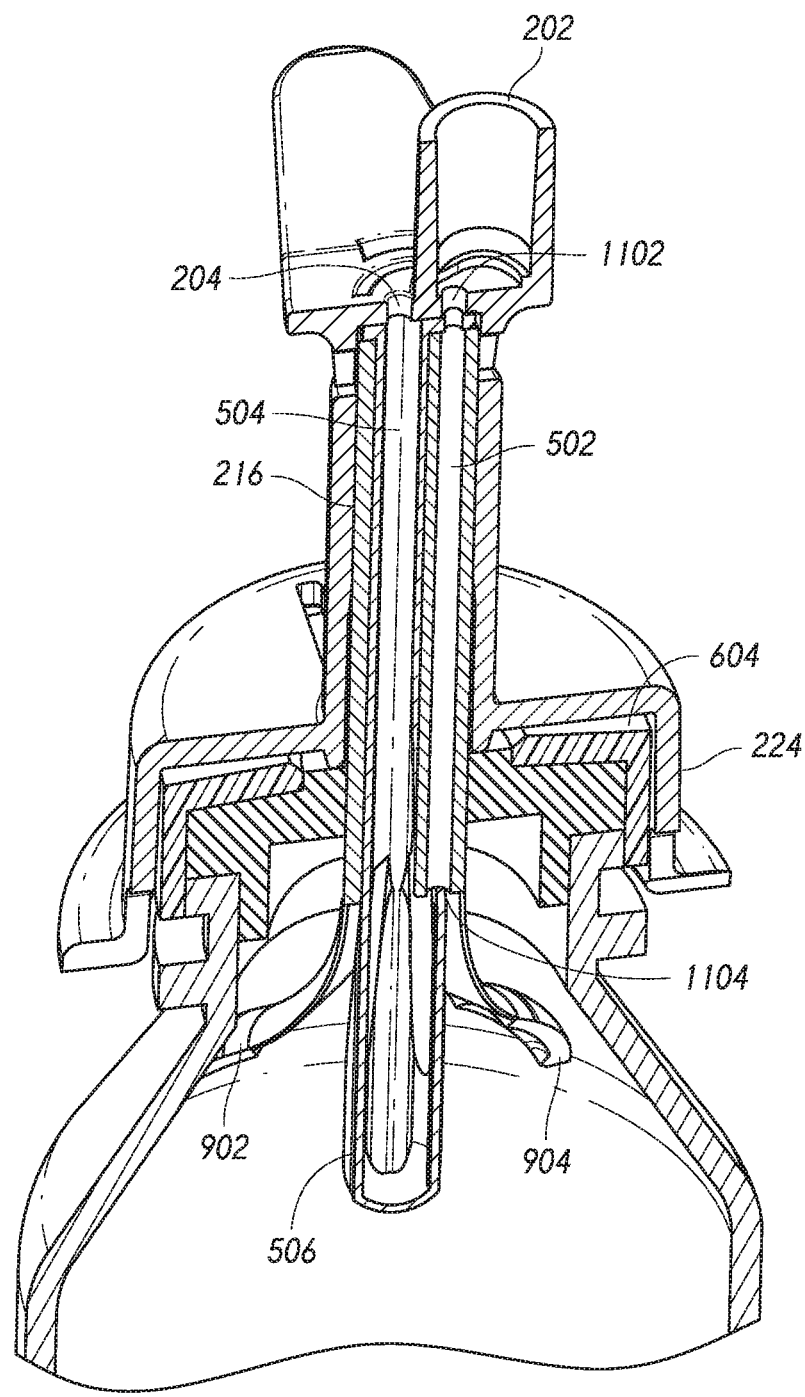
FIG. 11 is a partial cutaway view of one embodiment of a vial adaptor in a subsequent stage after it is coupled with a vial.

FIG. 11 a partial cutaway view of a vial adaptor 200 in a subsequent stage after it is coupled with a vial 600.

In the illustrated embodiment, the insertion member 216 comprises an extractor channel 502. The extractor channel 502 extends from a proximal extractor aperture 1102 to a distal extractor aperture 1104. As shown, the proximal extractor aperture 1102 is formed within both the proximal end of the insertion member 216 and the medical connector interface 202.

In the illustrated embodiment, the insertion member 216 also comprises a regulator channel 504 that terminates at the regulator aperture 204. As shown, the regulator aperture 204 is formed within both the proximal end of insertion member 216 and the handle 208. In some configurations, the regulator aperture 204 allows fluid communication between the ambient air and the interior of reservoir 506, which is within the regulator channel 504. In some embodiments, the regulator aperture 204 is slightly offset from an axial center of the adaptor 200. In some embodiments, the regulator aperture 204 is in close proximity (e.g., adjacent) to the medical connector interface 202. Advantageously, the regulator aperture 204 can be sufficiently small to prevent passage therethrough of undesirable objects, and sufficiently large to vent the reservoir 506 to atmosphere. A relatively small regulator aperture 204 can also permit the medical connector interface 202 to be located relatively centrally, thus helping to balance the adaptor 200 and prevent accidental tipping when the adaptor 200 is connected with a vial 600.

In various embodiments, the regulator aperture 204, the extractor aperture 1102, and the extractor aperture 1104 may have any shape, such as substantially circular, substantially square, substantially triangular, substantially polygonal, and so forth. As shown, the proximal extractor aperture 1102, the distal extractor aperture 1104, and the regulator aperture 204 are all substantially circular. In various instances, the diameter of each of these apertures may be between 10 percent to 80 percent, 20 percent to 60 percent, or 30 percent to 40 percent of the diameter of the insertion member 216. In some configurations, the diameter of each of these apertures may be between about 0.006 inches to 0.200 inches, between about 0.012 inches to 0.150 inches, or between about 0.018 inches to 0.100 inches.

In the illustrated embodiment, the adaptor 200 is coupled with a vial 600 and in a subsequent stage. The exterior of vial 600 may be assumed to be atmospheric pressure. Accordingly, in this subsequent stage the reservoir 506 is exposed to both the interior and exterior of the vial 600. The pressure between the exterior and the interior of the vial 600 will reach an equilibrium as the reservoir 506 expands and/or contracts.

The vial 600 and the adaptor 200 may be inverted to withdraw the contents of the vial 600. The distal extractor aperture 2104 can be seen as flush to the inner surface of the cap 604, which allows substantially all of the contents of the vial 600 to be withdrawn. The fluid is withdrawn from the vial 600 through the distal extractor aperture 2104 and through the extractor channel 502. That fluid may exit the extractor channel 502 through the proximal extractor aperture 1102 and into an exchange device, such as a syringe, coupled to the medical connector interface 202.

As the contents of the vial 600 are withdrawn, the effective volume of the vial 600 increases, thereby decreasing pressure within the vial 600. A decrease of pressure within the vial 600 increases the difference in pressure between the interior and exterior of the reservoir 506. More specifically, the interior of the reservoir 506 is exposed to the higher pressure outside the vial 600 and the other side of the reservoir 508 will be exposed to the lower pressure inside the vial 600. Consequently, air flows through the regulator aperture 204 and into the interior of the reservoir 506. This causes the reservoir 506 to expand to a new volume that compensates for the volume of the contents being withdrawn from the vial 600. In some embodiments, the composition of the reservoir 506 and/or the interface between the reservoir 506 and the interior of insertion member 216 may permit further expansion of the reservoir 506 axially and/or radially. Once the withdrawal of fluid from the vial 600 ceases, the system is again is again in equilibrium. Advantageously, the system operates near equilibrium to facilitate withdrawal of the contents of the vial 600.

In other instances, fluid may be injected into the vial 600, such as if a diluent is being added to the vial 600 or the user withdrew unwanted liquid (and/or air) from the vial 600. Fluid from the exchange device may enter the extractor channel 502 via the proximal extractor aperture 1102, and then it may enter the vial 600 via the distal extractor aperture 2104. As fluid is introduced to the vial 600 the pressure inside the vial 600 increases relative to the pressure surrounding the vial 600. Consequently, this causes the reservoir 506 to contract to a smaller volume to compensate for the volume of the returned fluid. This pressure difference also forces air from the interior of the reservoir 506 out through the regulator aperture 204, which reduces the pressure inside the vial 600. Because the system operates near equilibrium as the fluid and/or the air are injected into the vial 600, the pressure within the vial 600 does not significantly increase as the fluid and/or air is added to the vial 600.

Any channel, passageway, orifice, opening, or aperture in the adaptor 200 may include any number of filters and/or valves, including anti-reflux valves as described in U.S. Pat.

No. 8,409,164, titled "ANTI-REFLUX VIAL ADAPTORS", filed Aug. 19, 2009, which was previously incorporated by reference in the specification. For instance, any channel may include a filter and/or a valve—including channels such as the regulator channel 504 or the extractor channel 502. Any aperture may include a filter and/or a valve—including apertures such as the one or more regulator apertures (including, e.g., regulator aperture 204), or the one or more extractor apertures (including, e.g., proximal extractor aperture 1102 and distal extractor aperture 1104).

Figure 12:
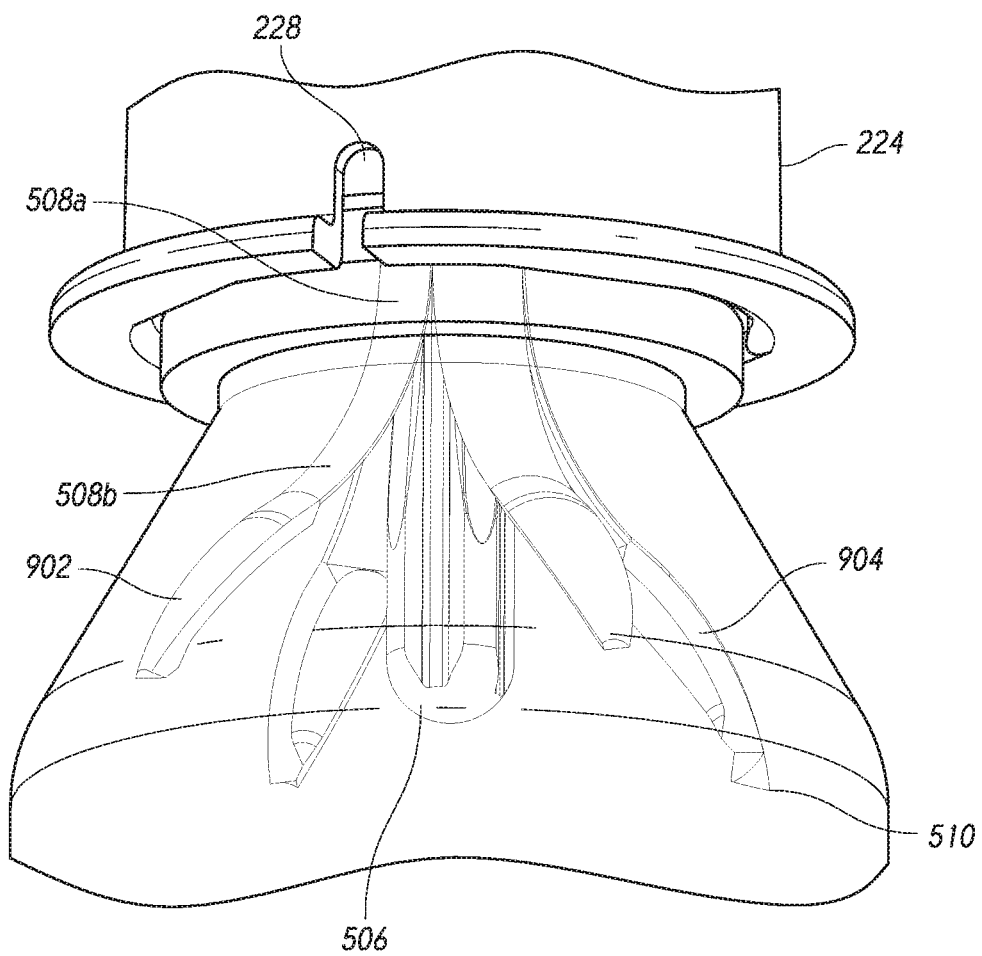
FIG. 12 is a partial perspective view of the tip of one embodiment of a vial adaptor in a subsequent stage after the vial adaptor is coupled with a vial.

FIG. 12 is a partial perspective view of the tip of a vial adaptor 200 in a subsequent stage after the vial adaptor 200 is coupled with a vial 600.

FIG. 12 provides a close up of the piercing member 508 in its open configuration. Clearly visible is a separate member 904 with a tip 510 and three separate members 902 which have no tip but are configured to fit flush against the tip 510 when all four separate members 902, 904 are in a closed configuration.

FIG. 12 also illustrates the role of recess 228 in the cap connector 224. In some configurations, the recess 228 may assist in signaling to a user the orientation of the extractor aperture 2104 when the adaptor 200 is coupled with a vial 600. For example, in some embodiments, a center of the extractor aperture 1104 and a center of recess 228 are substantially collinear along a straight line that is substantially perpendicular to a longitudinal axis of the insertion member 216. In certain of such embodiments, if the extractor aperture 1104 is obscured by the vial 600 and/or a portion of the cap connector 224 when the insertion member 216 is inside the vial 600, the radial orientation of the extractor aperture 1104 nevertheless can be determined by referencing the radial orientation of the recess 228, which is outside of the vial 600. In some embodiments, a method of extracting fluid from a vial 600 includes directing the recess 228 toward the ground to permit fluid to collect near the extractor aperture 1104.

Figure 13:
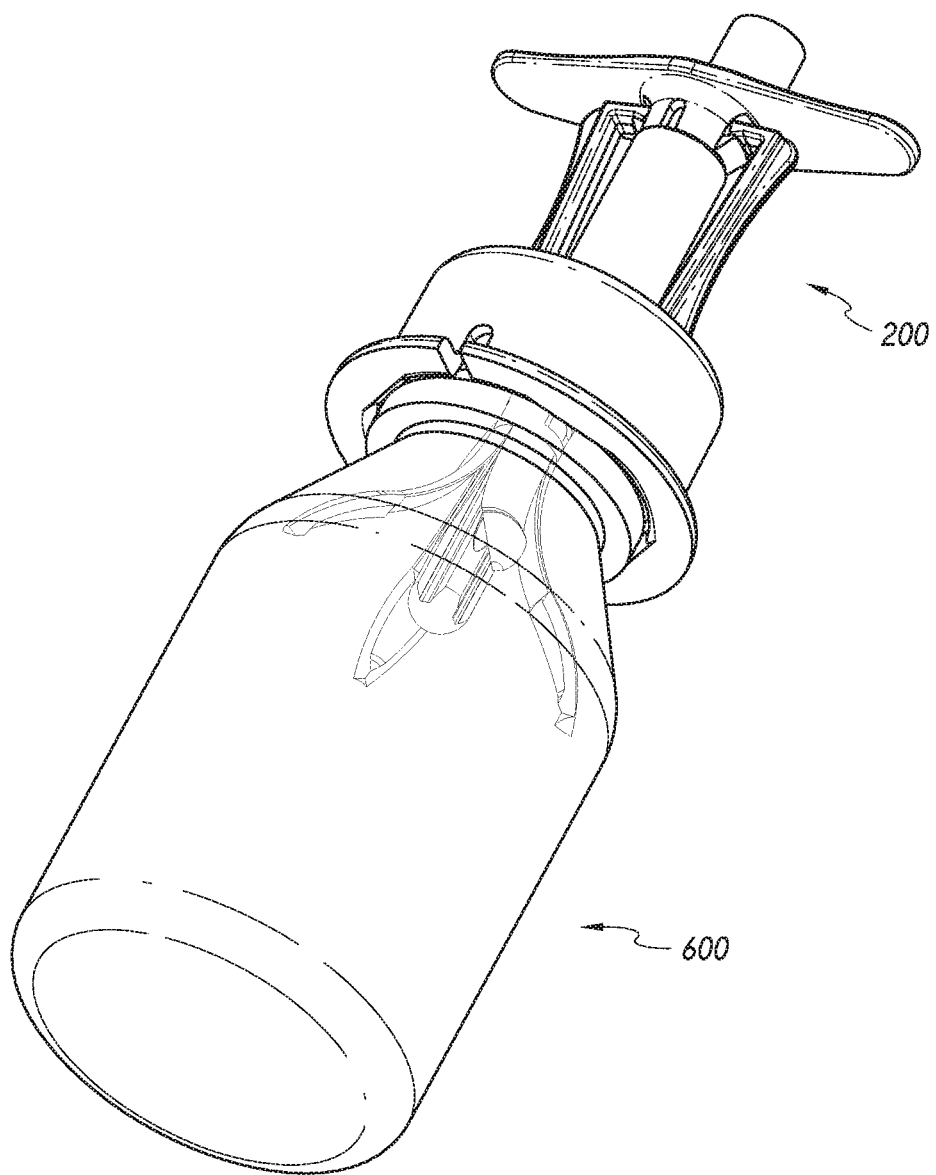
FIG. 13 is a perspective view of one embodiment of a vial adaptor in a subsequent stage after it is coupled with a vial.

FIG. 13 is a perspective view of a vial adaptor 200 in a subsequent stage after it is coupled with a vial 600.

Figure 14:
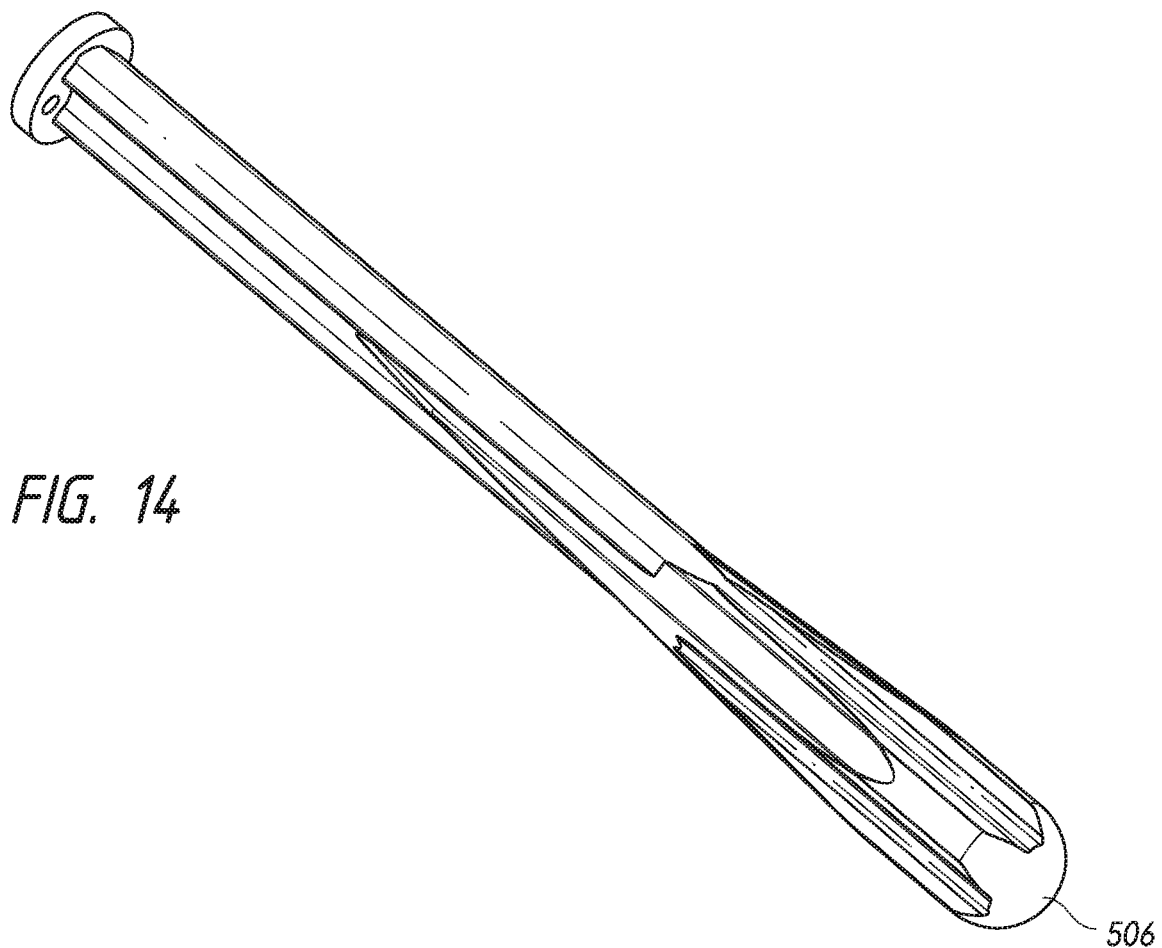
FIG. 14 is a perspective view of one embodiment of a reservoir.

FIG. 14 is a perspective view of one embodiment of a reservoir.

More specifically, the figure illustrates one embodiment of the reservoir 506 configured to fit within the insertion member 216.

Figure 15:
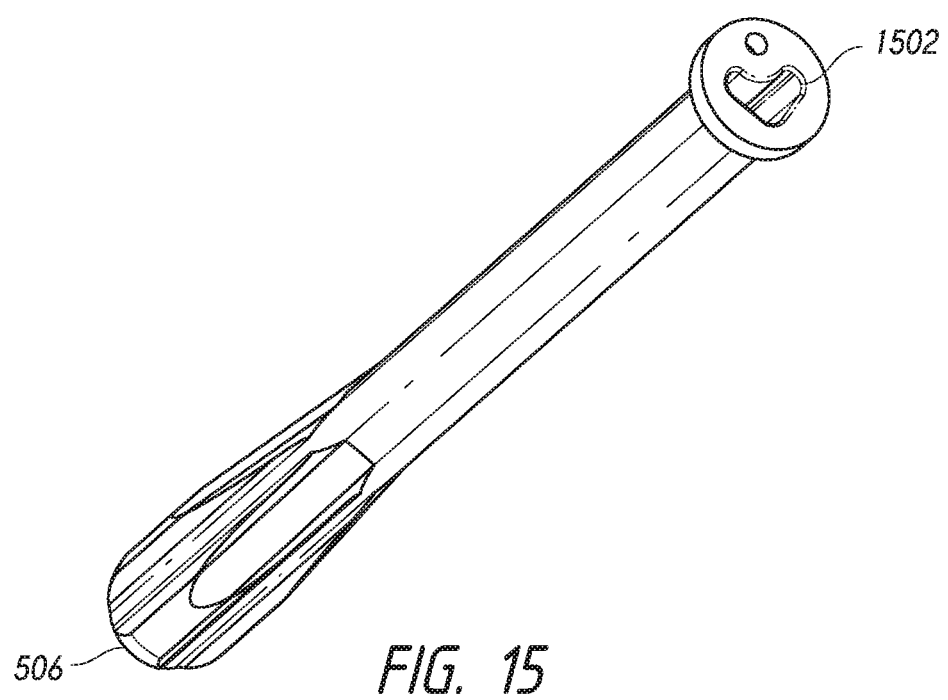
FIG. 15 is a perspective view of one embodiment of a reservoir.

In some embodiments, the reservoir 506 may have an elongate body with a closed distal end and a proximal end. The proximal end may also have a lip, which may be used for the purposes of securing the reservoir 506 to the adaptor 200. The proximal end may also have one or more openings, with at least one of the openings configured so that ambient air may flow through it. FIG. 15 shows a proximal end having two openings, but in the illustrated embodiment of FIG. 14 only one opening can be seen. This opening may provide passage for the extractor channel when the reservoir 506 is secured to the adaptor 200.

FIG. 15 is a perspective view of one embodiment of a reservoir.

This figure provides a better view of the proximal end of the reservoir 506, which is seen having two openings. The smaller, round opening may provide passage for the extractor channel when the reservoir 506 is secured to the adaptor 200. The dimensions of this smaller, round opening may be similar to the dimensions of the distal extractor aperture 1102 shown in FIG. 11.

The larger opening may be configured for allowing ambient air to flow through it. To regulate the pressure within a vial, ambient air may pass through this larger opening into the body of the reservoir 506, or ambient air may leave the body of the reservoir 506 out through the larger opening. This opening may have similar dimensions to the dimensions of the regulator aperture 204 shown in FIG. 11.

In some embodiments, the proximal end of the reservoir 506 may have a generally heart-shaped or horseshoe-shaped cross-section that the extractor channel can fit in, and which allows the distal end of the reservoir 506 to expand without blocking the distal extractor aperture 1104. The larger opening on the proximal end of the reservoir 506 may also have a generally heart-shaped or horseshoe-shaped opening to match the cross-section of the proximal end of the reservoir 506. As seen in the figure, the shape 1502 of the opening at the proximal end of the reservoir 506 is generally heart-shaped or horseshoe-shaped. This shape 1502 of the opening is associated with the cross-section of the reservoir 506 at the proximal end, which provides space for the extractor channel to fit next to the reservoir 506.

Some embodiments provide methods of using of the adaptor 200. Certain embodiments provide methods of manufacturing and assembling the various components of the adaptor 200.

During the manufacture or use of the adaptor 200, the adaptor 200 may have any feature or combination of features provided in the disclosure. For example, in some embodiments the adaptor 200 may include a housing and an insertion assembly. The housing may have any feature or combination of features discussed in this disclosure, and the insertion assembly may also have any feature or combination of features discussed in this disclosure.

In some embodiments, use of adaptor 200 may involve coupling the adaptor 200 to a vial 600. In some of such embodiments, coupling adaptor 200 to the vial 600 may involve coupling the cap connector 224 with the vial 600, such as by sliding the skirt of the cap connector 224 over the cap of the vial 600, which may deform the cap connector 224 and seat the projections 512 of the cap connector 224 against a feature of the vial 600—securing the adaptor 200 to the vial 600. When the adaptor 200 is fully coupled to the vial 600, the piercing member 508 is perpendicular to the septum of the vial 600 so that it can be inserted straight in to the vial 600. As used herein, the piercing member 508 is inserted "straight in" to the vial 600 if the path of insertion of the piercing member 508 (e.g., the path along which the piercing member 508 travels) is perpendicular to the septum of the vial 600, as opposed to the piercing member 508 being inserted into the septum via a path having an angle that substantially deviates from a normal vector of the septum.

Once the adaptor 200 is fully coupled to the vial 600, the engagement members 220 will disengage from the insertion member 216. For example, fully coupling the adaptor 200 to the vial 600 may trigger the engagement member unlock 230 mechanism by pressing the vial 600 against the protrusions 514. This may disengage the engagement members 220 from the notches 222 in the insertion member 216 in order to allow the insertion member 216 to slide along an insertion path. In some embodiments, the insertion path may be defined or bounded by the insertion member channel 218.

With the engagement members 220 disengaged from the insertion member 216 in order to allow the insertion member 216 to slide, a user may transition the adaptor 200 from the initial stage to the subsequent stage by sliding the insertion member 216 further into the insertion member channel 218 until the piercing member 508 enters the vial 600. The piercing member 508 enters the vial 600 straight in (and not at an angle), since the piercing member 508 was previously perpendicular against the septum of the vial and the insertion path of the insertion member 216 is also perpendicular to the septum of the vial as defined by the insertion member channel 218. Thus, the septum of the vial can only be punctured straight in. The user may continue sliding the insertion member 216 into the insertion member channel 218 until the engagement members 220 engage the locking ring 210 to prevent the insertion member 216 from being withdrawn or slid outwards from the insertion member channel 218.

At this point, the adaptor 200 will be in its subsequent stage. The piercing member 508 may change configurations in order to expose the reservoir 506. The contents of the vial may be withdrawn through the extractor channel 502 into a medical device connected to the medical device interface 202. The pressure within the vial may be regulated and maintained generally constant by allowing ambient air to enter the reservoir 506 through the regulator channel 504. Diluent may also be added to the vial via the extractor channel 502 using a medical device connected to the medical device interface 202. The pressure within the vial may be regulated and maintained generally constant by allowing ambient air to leave the reservoir 506 through the regulator channel 504.

In some embodiments, a method of using a vial access device may include coupling a housing to the vial, wherein the housing comprises an insertion path, and wherein the insertion assembly is configured to slide along the insertion path. The method of use may also include sliding the insertion assembly along the insertion path. The method of use may also optionally include sterilizing a piercing member of an insertion assembly by swabbing a tip of the piercing member with an alcohol wipe, wherein the piercing member is configured to pierce a septum of the vial. The method of use may also optionally include sterilizing the vial by swabbing the septum of the vial with an alcohol wipe. The method of use may also optionally include withdrawing a medicinal fluid from the vial.

In some embodiments, the insertion member 216, the locking ring 210, the handle 208, and the medical connector interface 202 are integrally formed of a unitary piece of material, such as polycarbonate plastic. In other embodiments, one or more of the insertion member 216, the locking ring 210, the handle 208, and the medical connector interface 202 comprise a separate piece. The separate pieces can be joined in any suitable manner, such as by glue, epoxy, ultrasonic welding, etc. Preferably, connections between joined pieces create substantially airtight bonds between the pieces. In further arrangements, any of the insertion member 216, the locking ring 210, the handle 208, and the medical connector interface 202 can comprise more than one piece.

In some embodiments, a method of manufacturing the adaptor 200 includes molding an insertion member channel 218, molding a cap connector 224, and attaching the insertion member channel 218 to the cap connector 224.

In other embodiments, the insertion member channel 218 and the cap connector 224 may be integrally formed, such that the method of manufacturing the adaptor 200 includes molding a cap connector 224 having an insertion member channel 218. In some of such embodiments, a method of manufacturing the adaptor 200 includes molding a cap connector 224 having an insertion member channel 218 and the engagement members 220.

In some embodiments, the method includes placing a seal within the cap connector 224. In some embodiments, the method includes placing a seal within the insertion member channel 218. In some of such embodiments, the method includes placing a seal between the insertion member channel 218 and the insertion member 216. In some embodiments, the method includes attaching a reservoir 506 to the insertion member 216. The reservoir 506 may be attached to the insertion member 216 by any suitable method described herein. However, in some embodiments the proximal end of the reservoir 506 may be adhered to the insertion member 216 to form a substantially fluid-tight seal therewith. Any suitable adhesive may be used, including cyanoacrylate.

In some embodiments, the method of assembling the adaptor 200 may include advancing a portion of the reservoir 506 into the insertion member 216. In some embodiments, the method includes attaching an end of the reservoir 506 to the insertion member 216, such as by applying adhesive to a lip of the reservoir 506 and adhering the lip of the reservoir 506 to an end of the insertion member 216. In some of such embodiments, the adhesive may be applied to the lip of the reservoir 506 through the openings 232. In some embodiments, the method includes advancing a piercing member 508 over the reservoir 506 and attaching the piercing member 508 to the insertion member 216.

It may be advantageous to manufacture the piercing member 508 separately from the insertion member 216 and attaching them together as compared to integrally forming the piercing member 508 and the insertion member 216 of a unitary piece of material. The insertion member 216 may be attached to the reservoir 506 to form a sub-assembly. The sub-assembly may be independently tested to determine whether a substantially fluid-tight seal has been formed between the reservoir 506 and the insertion member 216. An acceptable sub-assembly can then be attached to the piercing member 508 in any suitable manner, such as by ultrasonic welding. This may reduce the material costs of producing the material costs of producing an adaptor 200 by permitting disposal of only the sub-assembly should the reservoir 506 not seal properly with the insertion member 216.

In some embodiments, the method of assembling the adaptor 200 includes holding the piercing member 508 in a closed configuration while inserting the piercing member 508 into the insertion member channel 218. In some embodiments, the method of assembling includes advancing the piercing member 508 and the insertion member 216 further into the insertion member channel 218 until the engagement members 220 securely engages with the insertion member 216.

In some embodiments, a method for assembling the adaptor 200 includes lubricating the reservoir 506. For example, the method can include introducing or applying an amount of one or more of the lubricants to an exterior region of the reservoir 506. In some embodiments, the lubricant is applied before the reservoir 506 is secured to the insertion member 216.

In some embodiments, a method for assembling the adaptor 200 includes attaching a locking ring 210 to the end of the insertion member 216. In some embodiments, a method for assembling the adaptor 200 may further include attaching the handle 208 comprising a medical connector interface 202 to the end of the insertion member 216 with the seal 210.

Discussion of the various embodiments disclosed herein has generally followed the embodiments illustrated in the figures. However, the particular features, structures, or characteristics of any embodiments discussed herein may be combined in any suitable manner, as would be apparent to one of ordinary skill in the art from this disclosure, in one or more separate embodiments not expressly illustrated or described.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Thus, it is intended that the scope of the inventions herein disclosed should not be limited by the particular embodiments described above, but should be determined only by a fair reading of the claims that follow.

The following is claimed:

1. A vial access device for accessing contents of a vial, the device comprising:
   a needle-less connector comprising a flange to aid in coupling the vial access device with an exchange device or instrument used in extracting fluid from or injecting fluid into the vial;
   a housing comprising an engagement assembly configured to be coupled to the vial, wherein the engagement assembly comprises at least one of a cap connector, an adhesive, or tape;
   an insertion assembly comprising:
      a piercing member having an extractor aperture;
      an insertion member comprising the piercing member at a distal end of the insertion member;
      an insertion member channel having a proximal end; and
      a locking ring configured to engage with a protrusion at the proximal end of the insertion member channel, wherein the insertion member is configured to slide along the insertion member channel, and the piercing member is configured to pierce a septum of the vial;
   an extractor channel configured to connect the extractor aperture to the needle-less connector; and
   a regulator channel configured to permit fluid communication between an interior of the vial and ambient air,
   wherein the engagement assembly is configured to prevent the insertion member from sliding along the insertion member channel until the device is coupled to the vial;
   wherein the engagement assembly engages the locking ring when the insertion member is moved into a fully inserted position; and
   wherein the engagement assembly is configured to prevent the piercing member from piercing the septum of the vial until the device is coupled to the vial.

2. The device of claim 1, wherein the piercing member is perpendicular to the septum of the vial when the device is coupled to the vial.

3. The device of claim 1, wherein the piercing member abuts or partially pierces the septum of the vial when the device is coupled to the vial.

4. The device of claim 1, wherein the insertion member channel is perpendicular to the septum of the vial when the device is coupled to the vial.

5. The device of claim 1, wherein the piercing member can only pierce the septum of the vial straight in when the device is coupled to the vial.

6. The device of claim 1, wherein the engagement assembly is configured to engage the insertion assembly to prevent the insertion assembly from sliding along the insertion member channel.

7. The device of claim 1, wherein the engagement assembly is configured to disengage the insertion assembly to allow the insertion assembly to slide along the insertion member channel.

8. The device of claim 1, wherein the engagement assembly is engaged to the insertion assembly prior to the device being coupled to the vial.

9. The device of claim 8, wherein the engagement assembly comprises the cap connector, wherein the engagement assembly cannot disengage the insertion assembly until the cap connector is coupled to the vial.

10. The device of claim 8, wherein the engagement assembly disengages the insertion assembly when the device is coupled to the vial.

11. The device of claim 1, wherein the engagement assembly comprises one or more arms, wherein the one or more arms are configured to move between a first position and a second position.

12. The device of claim 11, wherein the one or more arms are further configured to engage the insertion assembly.

13. The device of claim 11, wherein the one or more arms are further configured to disengage the insertion assembly.

14. The device of claim 11, wherein the one or more arms engage the insertion assembly before the device is coupled to the vial.

15. The device of claim 11, wherein the one or more arms are in the first position before the device is coupled to the vial.

16. The device of claim 11, wherein the one or more arms move from the first position to the second position as the device is coupled to the vial.

17. The device of claim 11, wherein the one or more arms are in the second position when the device is coupled to the vial.

18. The device of claim 11, wherein the one or more arms disengage the insertion assembly as the one or more arms move from the first position to the second position.

19. The device of claim 1, wherein the device comprises a vial engagement assembly that allows the device to engage the vial in the direction of the piercing member.

20. The device of claim 1, further comprising a cap connector configured to couple the device to the vial.

21. The device of claim 1, wherein the extractor channel runs parallel to the insertion assembly.

22. The device of claim 1, configured such that the piercing member pierces the septum of the vial while the insertion assembly slides along the insertion member channel.

23. The device of claim 1, wherein the insertion assembly is maintained parallel to the insertion member channel by the engagement assembly.

24. The device of claim 1, configured such that sliding the insertion assembly along the insertion member channel towards the septum of the vial moves the insertion assembly into the fully inserted position.

25. The device of claim 24, wherein at least a portion of the piercing member is inside the vial when the insertion assembly is in the fully inserted position.

26. The device of claim 24, wherein the engagement assembly engages the insertion assembly when the insertion assembly is in the fully inserted position.

27. The device of claim 24, wherein one or more arms of the engagement assembly engage the insertion assembly when the insertion assembly is in the fully inserted position.

28. The device of claim 27, wherein the one or more arms of the engagement assembly are in the second position when the insertion assembly is in the fully inserted position.

29. The device of claim 24, wherein the engagement assembly keeps the piercing member inside the vial when the insertion assembly is in the fully inserted position.

30. The device of claim 24, wherein the engagement assembly prevents the insertion assembly from sliding along the insertion member channel away from the septum of the vial when the insertion assembly is in the fully inserted position.

31. The device of claim 24, wherein device produces a snap sound when the insertion assembly is moved into the fully inserted position.

* * * * *